US006531478B2

(12) United States Patent
Kordik et al.

(10) Patent No.: US 6,531,478 B2
(45) Date of Patent: Mar. 11, 2003

(54) AMINO PYRAZOLE DERIVATIVES USEFUL FOR THE TREATMENT OF OBESITY AND OTHER DISORDERS

(76) Inventors: Cheryl P. Kordik, 102 Summer Ridge Rd., Lansdale, PA (US) 19446; Scott L. Dax, 3 Quail Dr., Landenberg, PA (US) 19350; Chi Luo, 639 Broad St., Lansdale, PA (US) 19004; Allen B. Reitz, 109 Greenbriar Rd., Lansdale, PA (US) 19446; James J. McNally, 321 Heatherfield Dr., Souderton, PA (US) 18964; Timothy W. Lovenberg, 13252 Courtland Ter., San Diego, CA (US) 92101

( * ) Notice: Subject to any disclaimer, the term of this patent is extended or adjusted under 35 U.S.C. 154(b) by 0 days.

(21) Appl. No.: 09/791,203

(22) Filed: Feb. 22, 2001

(65) Prior Publication Data

US 2002/0065289 A1 May 30, 2002

Related U.S. Application Data

(60) Provisional application No. 60/184,550, filed on Feb. 24, 2000.

(51) Int. Cl.$^7$ .................. A61K 31/415; C07D 231/38; C07D 231/42
(52) U.S. Cl. .............. 514/275; 514/307; 514/310; 514/311; 514/314; 514/341; 514/404; 514/407; 544/331; 546/141; 546/143; 546/146; 546/147; 546/153; 546/162; 546/165; 546/168; 546/275.4; 548/371.4; 548/371.7; 548/372.5
(58) Field of Search ............... 544/331; 548/371.4, 548/371.7, 372.5; 546/172, 146, 174, 165, 138, 141, 143, 147, 153, 162, 168, 275.4; 514/404, 407, 275, 307, 310, 311, 314, 341

(56) References Cited

U.S. PATENT DOCUMENTS

| | | | |
|---|---|---|---|
| 3,198,791 A | 8/1965 | Weyer et al. | 260/239.9 |
| 3,592,890 A | 7/1971 | Janiak | 424/229 |
| 3,769,076 A | 10/1973 | Roth | 117/136 |
| 4,941,912 A | 7/1990 | Kristen et al. | 71/92 |
| 5,053,517 A | 10/1991 | Takigawa et al. | 548/376 |
| 5,202,441 A | 4/1993 | Takigawa et al. | 546/223 |
| 5,591,776 A | 1/1997 | Cavalla et al. | 514/622 |
| 5,668,151 A | 9/1997 | Poindexter et al. | 514/31 |
| 5,900,415 A | 5/1999 | Peterson et al. | 514/252 |
| 5,922,751 A | 7/1999 | Cavalla et al. | 514/407 |
| 5,922,884 A | 7/1999 | Huang et al. | 548/367.4 |
| 5,939,462 A | 8/1999 | Connell et al. | 514/665 |
| 6,020,357 A | 2/2000 | Pinto et al. | 514/406 |
| 6,107,322 A | 8/2000 | Huang et al. | 514/397 |
| 6,350,771 B1 * | 2/2002 | Wu et al. | 514/404 |

FOREIGN PATENT DOCUMENTS

| | | |
|---|---|---|
| EP | 0 350 176 B1 | 1/1990 |
| EP | 0 530 011 A1 | 3/1993 |
| EP | 0 839 810 A1 | 5/1998 |
| WO | WO 92/14456 | 9/1992 |
| WO | WO 96/00218 | 1/1996 |
| WO | WO 96/14307 | 5/1996 |
| WO | WO 00/69849 | 11/2000 |

OTHER PUBLICATIONS

CAPlus/CAOld Search Report (enlisting the compounds with RN Nos. 223518–57–8, 223518–67–0, and 223518–78–3 cited in the reference of Nam et al. Ivz. Timiryazevsk. S–kh. Akad., 1988).*

Nam et al. Ivz. Timiryazevsk. S–kh. Akad., (3), pp. 201–211, 1988.*

Wu et al., Chemical Abstracts, vol. 136:195652, 2002.*

Weintritt et al., Chemical Abstracts, vol. 133:4652, 2000.*

Uda et al., Chemical Abstracts, vol. 121:95825, 1994.*

Phillips et al., Chemical Abstracts, vol. 117:234010.*

Nagaoka et al., Chemical Abstracts, vol. 117:140489, 1992.*

Tachibana et al., Chemical Abstracts, vol. 111:15278, 1989.*

Boyd et al., Chemical Abstracts, vol. 86:43673, 1977.*

PCT Search Report mailed Nov. 16, 2001 PCT/US01/06025.

C. Cativiiela et al., Anales de Quimica; Institutode Quimica Medica Del C.S.I.C.; vol. 83, pp. 278–282I; Recibido el 3 de Jullo de 1986.

(List continued on next page.)

Primary Examiner—Richard L. Raymond
(74) Attorney, Agent, or Firm—Mary Appollina

(57) ABSTRACT

Amino pyrazole derivatives of the formula:

(I)

which are ligands for the neuropeptide Y, subtype 5 receptor and pharmaceutical compositions containing an amino pyrazole derivative as the active ingredient are described. The amino pyrazole derivatives are useful in the treatment of disorders and diseases associated with the NPY receptor subtype Y5.

20 Claims, No Drawings

OTHER PUBLICATIONS

P. A. Hipskind et al.; Annual Report in Medicinal Chemistry; Central Nervous System Diseases–31; pp 1–10, (1996).

G. Ege et al., J. Heterocyclic Chem., vol. 21, pp 689–695; (May–Jun. 1984).

H. A. El–Sherief et al.; J. Chem. Research (S) pp. 322–323 (1997).

K. Rudolf et al.; European Journal of Pharmacology 271; R11–R13 (1994).

C. S. Gal et al.; FEBS Letters 362—pp 192–196 (1995).

S. P. Watson et al.; Tetrahedro Letters, vo. 38, No. 52 pp 906509068 (1997).

J. Wright et al. Bioorganic & Medicinal Chemistry Letters, vol. 6, No. 15 pp 1809–1814 (1996).

\* cited by examiner

AMINO PYRAZOLE DERIVATIVES USEFUL FOR THE TREATMENT OF OBESITY AND OTHER DISORDERS

CROSS-REFERENCE TO RELATED APPLICATION

This application claims priority from U.S. provisional application Ser. No. 60/184,550, filed Feb. 24, 2000, the contents of which are hereby incorporated by reference.

FIELD OF THE INVENTION

This invention relates to a series of amino pyrazole derivatives, pharmaceutical compositions containing them and intermediates used in their preparation. The compounds of the invention are ligands for the neuropeptide Y subtype 5 (NPY5) receptor, a receptor which is associated with a number of central nervous system disorders and affective conditions.

BACKGROUND OF THE INVENTION

Regulation and function of the mammalian central nervous system is governed by a series of interdependent receptors, neurons, neurotransmifters, and proteins. The neurons play a vital role in this system, for when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to humans, neuropeptides have been discovered in a number of animal species. In some instances the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein that is enzymatically processed to yield the active substance. Based upon these differences, compared to small molecule neurotransmitters, neuropeptide-based strategies may offer novel therapies for CNS diseases and disorders. Specifically, agents that affect the binding of neuropeptides to their respective receptors or ameliorate responses that are mediated by neuropeptides are potential therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders and diseases have been treated with small molecules and peptides which modulate neuronal responses to endogenous neurotransmitters.

One example of the class of neuropeptides is neuropeptide Y (NPY). NPY was first isolated from porcine brain (Tatemoto, K. et al. *Nature* 1982, 296, 659) and was shown to be structurally similar to other members of the pancreatic polypeptide (PP) family such as peptide YY, which is primarily synthesized by endocrine cells in the gut, and pancreatic polypeptide, which is synthesized by the pancreas. Neuropeptide Y is a single peptide protein that consists of thirty-six amino acids containing an amidated C-terminus. Like other members of the pancreatic polypeptide family, NPY has a distinctive conformation that consists of an N-terminal polyproline helical region and an amphiphilic a-helix joined by a characteristic PP-fold (Vladimir, S. et. Al. *Biochemistry* 1990, 20, 4509). Furthermore, NPY sequences from a number of animal species have been elucidated and all show a high degree of amino acid homology to the human protein (>94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Six different receptor subtypes [Y1, Y2, Y3, Y4(PP), Y5, Y6 (formerly designated as a Y5 receptor)] are recognized today based upon binding profile, pharmacology and/or composition if identity is known (Wahlestedt, C. et. al. *Ann. NY Acad. Sci.* 1990, 611, 7; Larhammar, D. et. al. *J. Biol. Chem.* 1992, 267, 10935; Wahlestedt, C. et. al. *Regul. Pept,* 1986, 13, 307; Fuhlendorff, J. U. et. al. *Proc. Natl. Acad. Sci. USA* 1990, 87, 182; Grundemar, L. et. al. *J. Pharmacol. Exp. Ther.* 1991, 258, 633; Laburthe, M. et. al. *Endocrinology* 1986, 118, 1910; Castan, I. et. al. *Endocrinology* 1992, 131, 1970; Gerald, C. et. al. *Nature* 1996, 382, 168; Weinberg, D. H. et. al. *Journal of Biological Chemistry* 1996, 271, 16435; Gehlert, D. et. al. *Current Pharmaceutical Design* 1995, 1, 295; Lundberg, J. M. et. al. *Trends in Pharmaceutical Sciences* 1996, 17, 301). Most and perhaps all NPY receptor proteins belong to the family of so-called G-protein coupled receptors (GPCRs). The neuropeptide Y5 receptor, a putative GPCR, is negatively coupled to cellular cyclic adenosine monophosphate (cAMP) levels via the action of adenylate cyclase (Gerald, C. et. al. *Nature* 1996, 382, 168; Gerald, C. et. al. PCT WO 96/16542). For example, NPY inhibits forskolin-stimulated cAMP production/levels in a neuroblastoma cell line. A Y5 ligand that mimics NPY in this fashion is an agonist whereas one that competitively reverses the NPY inhibition of forskolin-stimulated cAMP production is an antagonist.

Neuropeptide Y itself is the archetypal substrate for the NPY receptors and its binding can elicit a variety of pharmacological and biological effects in vitro and in vivo. When administered to the brain of live animals (intracerebroventricularly (icv) or into the amygdala), NPY produces anxiolytic effects in established animal models of anxiety such as the elevated plus-maze, Vogel punished drinking and Geller-Seifter's bar-pressing conflict paradigms (Heilig, M. et. al. *Psychopharmacology* 1989, 98, 524; Heilig, M. et. al. *Reg. Peptides* 1992, 41, 61; Heilig, M. et. al. *Neuropsycho-pharmacology* 1993, 8, 357). Thus compounds that mimic NPY are postulated to be useful for the treatment of anxiolytic disorders.

The immunoreactivity of neuropeptide Y is notably decreased in the cerebrospinal fluid of patients with major depression and those of suicide victims (Widdowson, P. S. et. al. *Journal of Neurochemistry* 1992, 59, 73), and rats treated with tricyclic antidepressants display significant increases of NPY relative to a control group (Heilig, M. et. al. *European Journal of Pharmacology* 1988, 147, 465). These findings suggest that an inadequate NPY response may play a role in some depressive illnesses, and that compounds that regulate the NPY-ergic system may be useful for the treatment of depression.

Neuropeptide Y improves memory and performance scores in animal models of learning (Flood, J. F. et. al. *Brain Research* 1987, 421, 280) and therefore may serve as a cognition enhancer for the treatment of neurodegenerative diseases such as Alzheimer's Disease (AD) as well as AIDS-related and senile dementia.

Elevated plasma levels of NPY are present in animals and humans experiencing episodes of high sympathetic nerve activity such as surgery, newborn delivery and hemorrhage (Morris, M. J. et. al. *Journal of Autonomic Nervous System* 1986, 17, 143). Thus chemical substances that alter the NPY-ergic system may be useful for alleviating the condition of stress.

Neuropeptide Y also mediates endocrine functions such as the release of luteinizing hormone (LH) in rodents (Kalra, S. P. et. al. *Frontiers in Neuroendrocrinology* 1992, 13, 1). Since LH is vital for mammalian ovulation, a compound that mimics the action of NPY could be useful for the treatment of infertility, particularly in women with so-called luteal phase defects.

Neuropeptide Y is a powerful stimulant of food intake; as little as one-billionth of a gram, when injected directly into the CNS, causes satiated rats to overeat (Clark, J. T. et. al. *Endocrinology* 1984, 115, 427; Levine, A. S. et. al. *Peptides* 1984, 5, 1025; Stanley, B. G. et. al. *Life Sci.* 1984, 35, 2635; Stanley, B. G. et. al. *Proc. Nat. Acad. Sci. USA* 1985, 82, 3940). Thus NPY is orexigenic in rodents but not anxiogenic when given intracerebroventricularly and so antagonism of neuropeptide receptors may be useful for the treatment of eating disorders such as obesity, anorexia nervosa and bulimia nervosa.

In recent years, a variety of potent, structurally distinct small molecule Y1 antagonists has been discovered and developed (Hipskind, P. A. et. al. *Annu. Rep. Med. Chem.* 1996, 31, 1–10; Rudolf, K. et. al. *Eur. J. Pharmacol.* 1994, 271, R11; Serradeil-Le Gal, C. et. al. *FEBS Lett.* 1995, 362, 192; Wright, J. et. al. *Bioorg. Med. Chem. Lett.* 1996, 6, 1809; Poindexter, G. S. et. al. U.S. Pat. No. 5,668,151; Peterson, J. M. et. al. WO9614307 (1996)). However, despite claims of activity in rodent models of feeding, it is unclear if inhibition of a feeding response can be attributed to antagonism of the Y1 receptor.

Several landmark studies strongly suggest that an "atypical Y1" receptor and/or the Y5 receptor, rather than the classic Y1 receptor, is responsible for invoking NPY-stimulated food consumption in animals. It has been shown that the NPY fragment NPY2–36 is a potent inducer of feeding despite poor binding at the classic Y1 receptor (Stanley, B. G. et. al. *Peptides* 1992, 13, 581). Conversely, a potent and selective Y1 agonist has been reported to be inactive at stimulating feeding in animals (Kirby, D. A. et. al. *J. Med. Chem.* 1995, 38, 4579). More pertinent to the invention described herein, [D-Trp$^{32}$]NPY, a selective Y5 receptor activator has been reported to stimulate food intake when injected into the hypothalamus of rats (Gerald, C. et. al. *Nature* 1996, 382, 168). Since [D-Trp$^{32}$]NPY appears to be a full agonist of the Y5 receptor with no appreciable Y1 activity, the Y5 receptor is hypothesized to be responsible for the feeding response. Accordingly compounds that antagonize the Y5 receptor should be effective in inhibiting food intake, particularly that stimulated by NPY.

Sulfanilamidopyrazoles used in hypoglycemic compositions are disclosed in Belgian Patent 655,242 and GB Patent No. 1,054,278. 3,4-substituted pyrazoles as inhibitors of phosphodiesterase are disclosed by Cavalla et al., in PCT WO 96/00218. Nitrogen containing heteroaromatics as factor Xa inhibitors are disclosed by Pinto et al., in PCT WO 98/28269, while Shapiro, H. K., in PCT WO 92/14456 discloses the use of pyrazole derivatives in pharmaceuticals for the treatment of neurological disorders. Certain 1-tolylsulfonyl-pyrazole derivatives are described by Nam, et al. (*Izv. Timityazevsk. S-kh. Akad.* 1998, 3,201).

1-phenyl substituted aminopyrazole derivatives and their Tensmeyer substituent increments for NMR spectral profiles are described by Ege, G. and Franz, H, J. (*Heterocyclic Chem.*, 1984, 21, 689) and Cativeiela, et al. (*Anales De Quimica*, 1987, 83, 278). The synthesis of 5-substituted aminopyrazole derivatives is described by Watson, S. P., et al. (*Tetrahedron Letters*, 1997, 38 (52), 9065). Takigawa et al., in EP 0350176 disclose a method for the synthesis of pyrazolecarboxylic acid and derivatives, while El-Sherief et al. (*J. Chem. Res., Synop.* 1997, 9, 322) describe the synthesis of 2-(5-amino-3-arylpyrazol-1-yl)-3-methylquinoxalines.

Substituted amino pyrazole derivatives useful as herbicides are disclosed by Kirsten, et al., in U.S. Pat. No. 4,941,912. Pesticidal 1-polyarylpyrazoles are disclosed by Herman, et al. in EP 0839810. Janiak, M. in U.S. Pat. No. 3,592,890 discloses the use of 5-(para-aminobenzenesulfonylamido)-1-phenyl-3-methyl-pyrazole for combating atrophic rhinitis as a prophylactic veterinary method. Weyer et al., in U.S. Pat. No 3,198,791 disclose sulfanilamidopyrazole derivatives and a process for their preparation. Roth, S. H., in U.S. Pat. No. 3,769,076 discloses intumescent compositions containing arylsulfonylaminopyrazoles and imidazoles. Substituted aminopyrazoles as components in silver halide colour photographic light sensitive material are disclosed by Kida et al., in EP 0530011.

SUMMARY OF THE INVENTION

The present invention provides novel amino pyrazole derivative compounds useful as ligands of the neuropeptide Y, subtype 5 receptor. More particularly, the present invention is directed to compounds of the general of the formula (I):

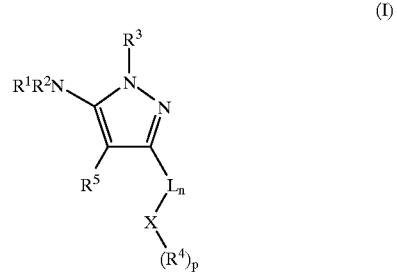

wherein $R^1$ and $R^2$ are each independently selected from the group consisting of hydrogen, $C_1$–$C_6$alkyl, sulfonylamino, and unsubstituted or substituted arylsulfonyl; wherein the substituents on the arylsulfonyl are one or more substituents independently selected from halogen, $C_1$–$C_6$alkyl, $C_1$–$C_6$alkoxy, trifluoromethyl or trifluoromethoxy;

R³ is selected from the group consisting of unsubstituted or substituted aryl and unsubstituted or substituted heteroaryl; wherein the substituents on the aryl or heteroaryl are one or more substituents independently selected from halogen, $C_1$–$C_6$alkyl, $C_1$–$C_6$alkoxy, trifluoromethyl, trifluoromethoxy, amino, $C_1$–$C_6$alkylamino or di($C_1$–$C_6$alkyl)amino;

L is selected from the group consisting of unsubstituted or substituted aryl, unsubstituted or substituted heteroaryl and $C_3$–$C_8$cycloalkyl; wherein the substituents on the aryl or heteroaryl are one or more substituents independently selected from halogen, $C_1$–$C_4$alkyl or trifluoromethyl;

n is an integer selected from 0 or 1;

X is selected from the group consisting of sulfonylamino, aminocarbonyl, carbonyl, carbonylamino, sulfonyl,

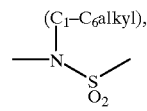

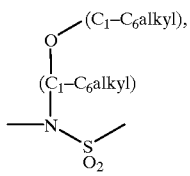

sulfonylamino$C_1$–$C_6$alkyl, $C_1$–$C_6$alkylaminosulfonyl, and di(unsubstituted or substituted arylsulfonyl)amino; wherein the substituents on the aryl group are one or more substituents independently selected from halogen, $C_1$–$C_6$alkyl, $C_1$–$C_6$alkoxy, trifluoromethyl, trifluoromethoxy, $C_1$–$C_6$alkylcarbonylamino, amino, $C_1$–$C_6$alkylamino or di($C_1$–$C_6$alkyl)amino, and wherein the two aryl groups of the di(unsubstituted or substituted arylsulfonyl)amino have the same substitution pattern;

R⁴ is selected from the group consisting of hydrogen, $C_1$–$C_6$alkyl, unsubstituted or substituted aryl, $C_1$–$C_6$aralkyl, unsubstituted or substituted heteroaryl and unsubstituted or substituted heterocycloalkyl; wherein the substituents on the aryl, heteroaryl or heterocycloalkyl are one or more substituents independently selected from halogen, $C_1$–$C_6$alkyl, $C_1$–$C_6$alkoxy, trifluoromethyl, trifluoromethoxy, amino, $C_1$–$C_6$alkylamino, di($C_1$–$C_6$alkyl)amino, nitro or cyano;

p is an integer selected from 0 or 1;

R⁵ is selected from the group consisting of hydrogen, halogen, $C_1$–$C_4$alkyl and trifluoromethyl;

provided that when X is di(unsubstituted or substituted arylsulfonyl)amino then p is 0; and provided that when R¹ and R⁵ are both hydrogen, and R³ is phenyl, or methylphenyl, and n is 1, and L is phenyl, and X is sulfonylamino, and R² is methylphenylsulfonyl, then R⁴ is selected from the group consisting of hydrogen, $C_1$–$C_6$alkyl, unsubstituted or substituted aryl, wherein the substituents on the aryl are one or more substituents independently selected from halogen, $C_2$–$C_6$alkyl, $C_1$–$C_6$alkoxy, trifluoromethyl, trifluoromethoxy, amino, $C_1$–$C_6$alkylamino, di($C_1$–$C_6$alkyl)amino, nitro or cyano; $C_1$–$C_6$aralkyl, unsubstituted or substituted heteroaryl and unsubstituted or substituted heterocycloalkyl; wherein the substituents on the heteroaryl or heterocycloalkyl are one or more independently selected from halogen, $C_1$–$C_6$alkyl, $C_1$–$C_6$alkoxy, trifluoromethyl, trifluoromethoxy, amino, $C_1$–$C_6$alkylamino, di($C_1$–$C_6$alkyl)amino, nitro or cyano; [in other words, when R¹ and R⁵ are both hydrogen, and R³ is phenyl or methylphenyl, and n is 1, and L is phenyl, and X is sulfonylamino, and R² is methylphenylsulfonyl, then R⁴ is not methylphenyl];

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention is a method of treating a condition mediated by the NPY Y5 receptor in a subject in need thereof comprising administering to the subject a therapeutically effective amount of any of the compounds or pharmaceutical compositions described above.

An example of the invention is a method for treating a condition selected from eating disorder, obesity, bulimia nervosa, diabetes, binge eating, anorexia nervosa, dyslipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea in a subject in need thereof comprising administering to the subject an effective amount of any of the compounds or pharmaceutical compositions described above.

Further illustrating the invention is the use of a compound of formula (I) in the preparation of a medicament for treating conditions mediated by the NPY Y5 receptor.

DETAILED DESCRIPTION OF THE INVENTION

The present invention provides novel amino pyrazole derivative compounds useful as ligands of the neuropeptide Y, subtype 5 receptor. More particularly, the present invention is directed to compounds of the general of the formula (I):

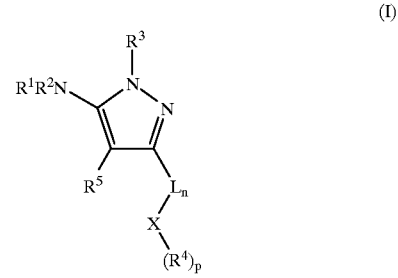

(I)

wherein R¹, R² R³, R⁴, R⁵, L, X, n and p are as previously defined, and pharmaceutically acceptable salts thereof.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The amino pyrazoles of formula (I) that comprise this invention may be synthesized via the routes outlined in Schemes 1–7, described in more detail below.

Compounds of formula (I) wherein X is -sulfonylamino- and L is -phenyl-, may be prepared according to the process outlined in Scheme 1.

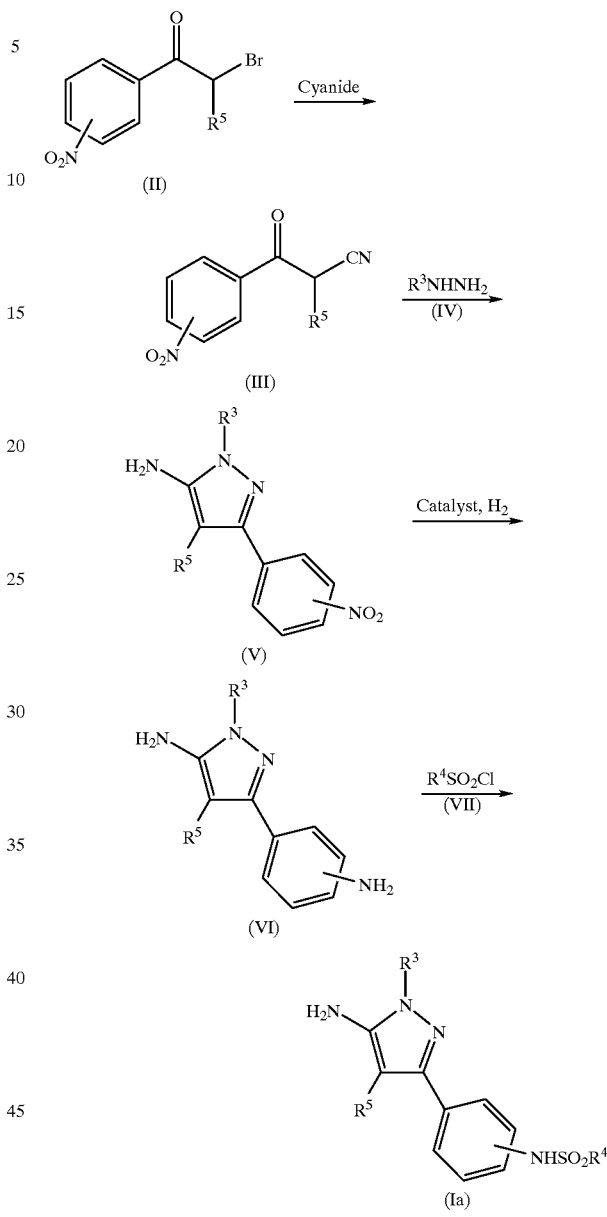

More specifically, a suitably substituted α-bromoketone of formula (II), a known compound or compound prepared by known methods, is reacted with cyanide, in the presence of an alcoholic solvent such as ethanol, methanol, and the like, with heating from ambient temperature to reflux, to afford the corresponding α-cyanoketone of formula (III).

The α-cyanoketone of formula (III) is coupled with a suitably substituted hydrazine of formula (IV), in the presence of a base such as triethylamine (TEA), diisopropylethylamine (DIPEA), and the like, in an alcoholic solvent such as ethanol, methanol, and the like, with heating from ambient temperature to reflux, to provide the corresponding pyrazole of formula (V).

The pyrazole of formula (V) is treated with hydrogen gas, which gas is applied at a pressure in the range of ambient to 100 p.s.i., in an inert hydrocarbon, ethereal or alcohol solvent, such as methanol, ethanol, and the like, in the presence of a catalyst such as palladium on carbon, platinum oxide, Raney nickel, and the like, with heating from ambient temperature to reflux, to yield the corresponding compound of formula (VI).

The compound of formula (VI) is coupled with a suitably substituted sulfonyl chloride of formula (VII), in the presence of a base such as potassium carbonate, cesium carbonate, and the like, in the presence of water and an ethereal solvent such as THF, diethyl ether and the like, to provide the corresponding aminopyrazole of formula (Ia).

To prepared compounds of formula (I) wherein X is

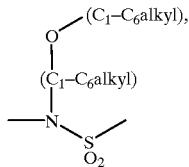

the compound of formula (Ia) may be further reacted with a halogenated $(C_1-C_6 alkyl)(C_1-C_6 alkyl)$ether and a phase transfer catalyst such as benzyl triethyl ammonium chloride, in the presence of water, in the presence of a base such as potassium carbonate, cesium carbonate, and the like, in a halogenated organic solvent such as methylene chloride, chloroform and the like.

Alternatively, the compound of formula (VI) may be reacted to prepare a compound of formula (I) wherein X is di(substituted sulfonyl)imino- and L is -phenyl-, according to Scheme 2.

SCHEME 2

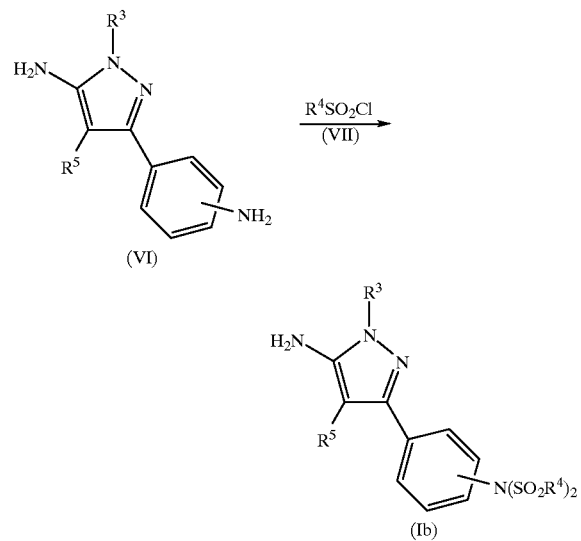

Accordingly, the compound of formula (VI) is reacted with a suitably substituted sulfonyl chloride of formula (VII), in the presence of at least one equivalent, preferably about three equivalents, of a base such as triethylamine, diisopropylethylamine, and the like, and a halogenated solvent such as methylene chloride, carbon tetrachloride, and the like, with heating from ambient temperature to reflux, to afforded the corresponding aminopyrazole of formula (Ib).

Alternatively, the compound of formula (VI) may be reacted to prepare a compound of formula (I) wherein X is -carbonylamino- and L is -phenyl-, according to the process outline in Scheme 3.

SCHEME 3

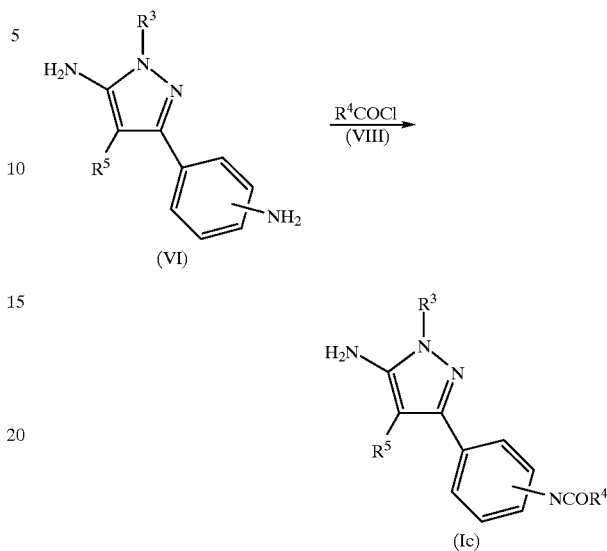

Accordingly, the compound of formula (VI) is reacted with an acylating reagent such as an acid chloride of formula (VIII), in the presence of halogenated organic solvent such as methylene chloride, carbon tetrachloride, and the like, to yield the corresponding aminopyrazole of formula (Ic).

Compounds of formula (I) wherein X is -sulfonylamino-, L is -phenyl- and $R^4$ is a mono- or di-substituted aminophenyl, may be prepared according to the process outlined in Scheme 4.

SCHEME 4

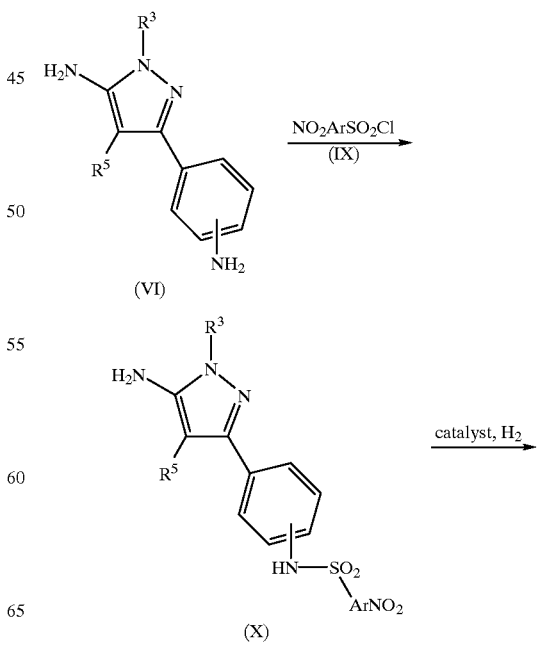

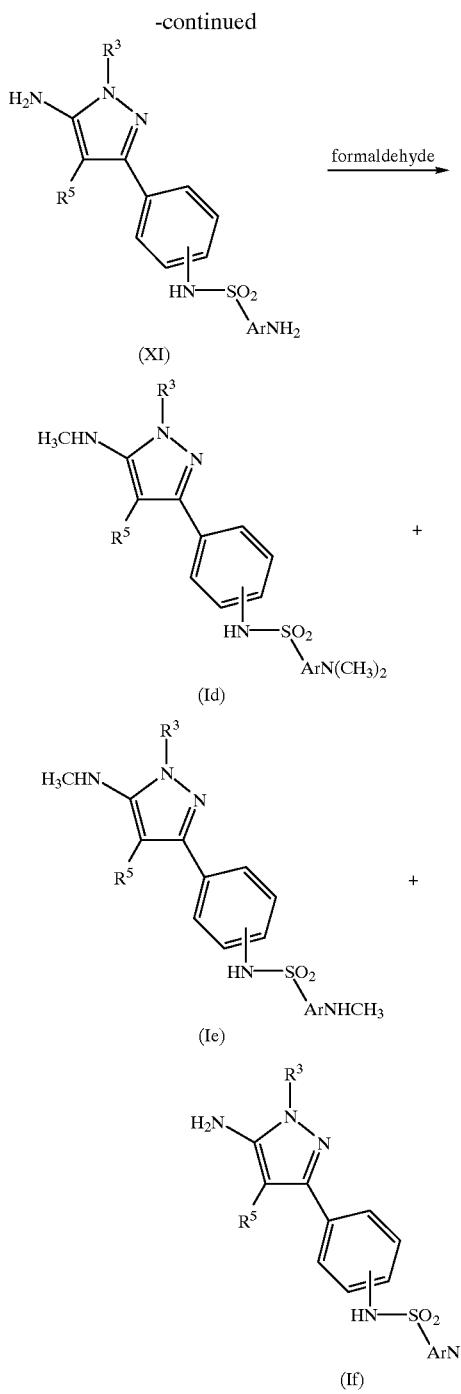

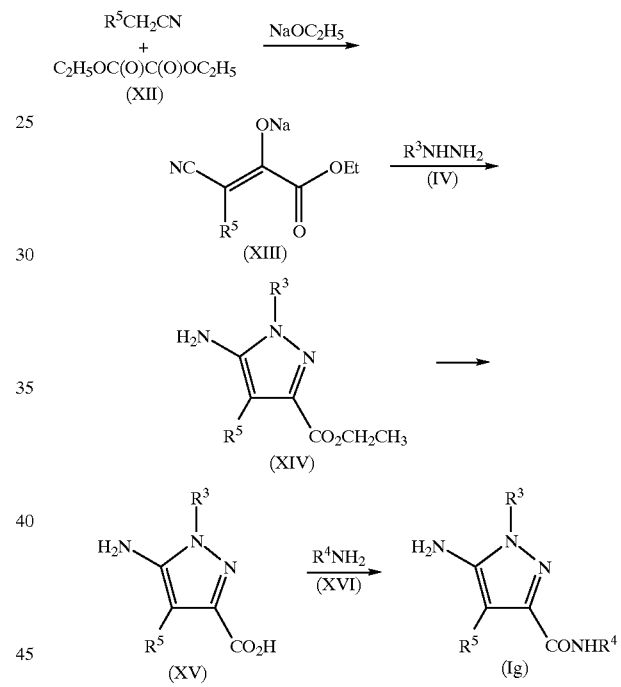

ethanol, and the like, with heating from ambient temperature to reflux, to yield the corresponding compound of formula (XI).

The compound of formula (XI) is reacted with formaldehyde, in acetonitrile, in the presence of an acid such as acetic acid, and the like, and in the presence of a reducing agent such as sodium cyanoborohydride, sodium tetracetoxyborohydride, and the like, to afford a mixture of the corresponding methylated aminopyrazoles, compounds of formula (Id), (Ie) and (If), respectively. Preferably, the compounds of formula (1d), (le) and (If) are separated by known methods, such as flash chromatography.

Compounds of formula (I) wherein X is -aminocarbonyl- and n is 0 (such that L is absent), may be prepared according to the process as outlined in Scheme 5.

More specifically, the compound of formula (VI) is reacted with a nitro substituted aryl sulfonyl chloride of formula (IX), wherein Ar represents an aryl group, in the presence of base such as potassium carbonate, cesium carbonate, and the like, and an aqueous ethereal solvent such as aqueous THF, and the like, with heating from at ambient temperature to reflux, to yield the corresponding compound of formula (X).

The compound of formula (X) is reacted with hydrogen gas, at a pressure in the range of ambient to 100 p.s.i., preferably at a pressure between 40–50 p.s.i., in the presence of a suitable catalyst such as palladium on carbon, platinum oxide, and the like, in an inert hydrocarbon, ethereal ester or alcohol solvent, such as hexane, ethyl acetate, methanol, Accordingly, a suitably substituted compound of fotrmula (XII), a known compound or compound prepared by known methods, is reacted with diethyl oxalate, in the presence of a base such as sodium ethoxide, sodium methoxide, and the like, in an ethereal solvent such as diethyl ether, tetrahydrofuran, and the like, at a temperature between 0° C. and ambient temperature, preferably at about 0° C., to yield the corresponding compound of formula (XIII).

The compound of formula (XIII) is reacted with a suitably substituted hydrazine of formula (IV), in an aqueous halogenated solvent such as aqueous carbon tetrachloride, methylene chloride, and the like, in the presence of an acid such as sulfuric acid, hydrochloric acid, and the like, to afford the corresponding amino pyrazole ester of formula (XIV).

The amino pyrazole ester of formula (XIV) is hydrolyzed using a base such as aqueous sodium hydroxide, lithium hydroxide, and the like, in an aqueous alcohol such as aqueous ethanol, methanol, and the like, with heating from ambient temperature to reflux, to afford the corresponding carboxylic acid of formula (XV).

The carboxylic acid of formula (XV) is coupled to a suitably substituted amine of formula (XV), in the presence of a coupling reagent such as HATU, and the like, in the presence of a sterically hindered amine such as diisopropylethylamine (DIPEA), triethylamine (TEA), and the like, in a solvent such as DMF, and the like, at ambient temperature, to produce the corresponding aminopyrazole of formula (Ig).

Compounds of formula (I) wherein X is -aminocarbonyl-, L is -phenyl- and $R^1$ is hydrogen or phenylsulfonyl and $R^2$ is phenylsulfonyl, may be prepared according to the process outlined in Scheme 6.

SCHEME 6

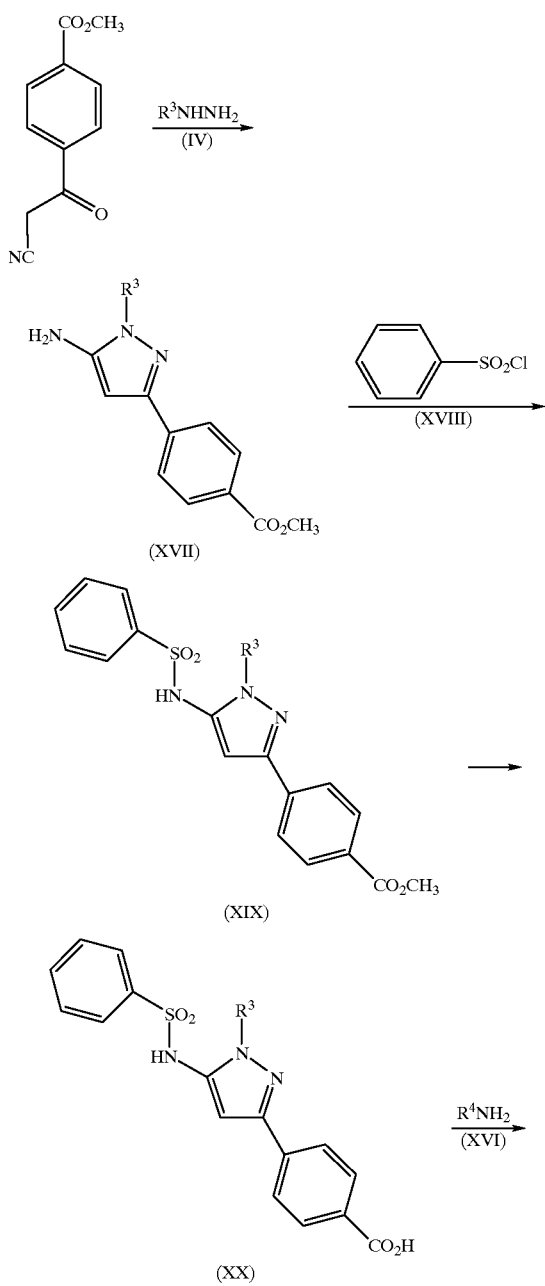

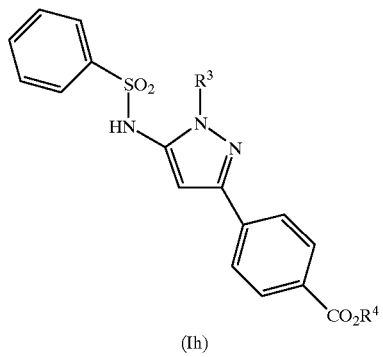

More specifically, methyl-4-(cyanoacetyl) benzoate is reacted with a suitably substituted hydrazine of formula (IV), in an alcoholic solvent such as ethanol, methanol, and the like, with heating from ambient temperature to reflux, to yield the corresponding compound of formula (XVII).

The compound of formula (XVII) is reacted with phenylsulfonyl chloride of formula (XVIII), in a halogentaed organic solvent such as methylene chloride, carbon tetrachloride, and the like, in the presence of pyridine, to yield the corresponding compound of formula (XIX).

The compound of formula (XIX) is hydrolyzed in the presence of an aqueous base such as sodium hydroxide, lithium hydroxide, and the like, to produce the corresponding carboxylic acid of formula (XX).

The compound of formula (XX) is coupled with a suitably substituted amine of formula (XVI), in the presence of a coupling agent such as HATU, and the like, in a base such as diisopropylethylamine (DIPEA), triethylamine (TEA), and the like, in the presence of a reagent such as HOBT and DMAP, and the like, to afford the corresponding aminopyrazole of formula (Ih).

In compounds of formula (I) wherein $R^4$ is a cyclic secondary amine, the compound of formula (XX) is coupled directly with the cyclic secondary amine, in the presence of a coupling agent such as HATU, and the like, in a base such as diisopropylethylamine (DIPEA), triethylamine (TEA), and the like, in the presence of a regent such as HOBT and DMAP, and the like, to produce the corresponding compound of formula (I).

For compounds of formula (I) wherein $R^1$ and $R^2$ are both phenylsulfonyl, the compound of formula (XVII) is reacted with at least two equivalents of the phenylsulfonyl chloride of formula (XVIII) to yield the corresponding bis (phenylsulfonyl)amino substituted compound of formula (XIX) Compounds of formula (I) wherein L is -phenyl- or -cyclohexyl- and X is -sulfonylaminoalkyl-, wherein the amino group may be optionally substituted, may be produced according to the process outlined in Scheme 7.

SCHEME 7

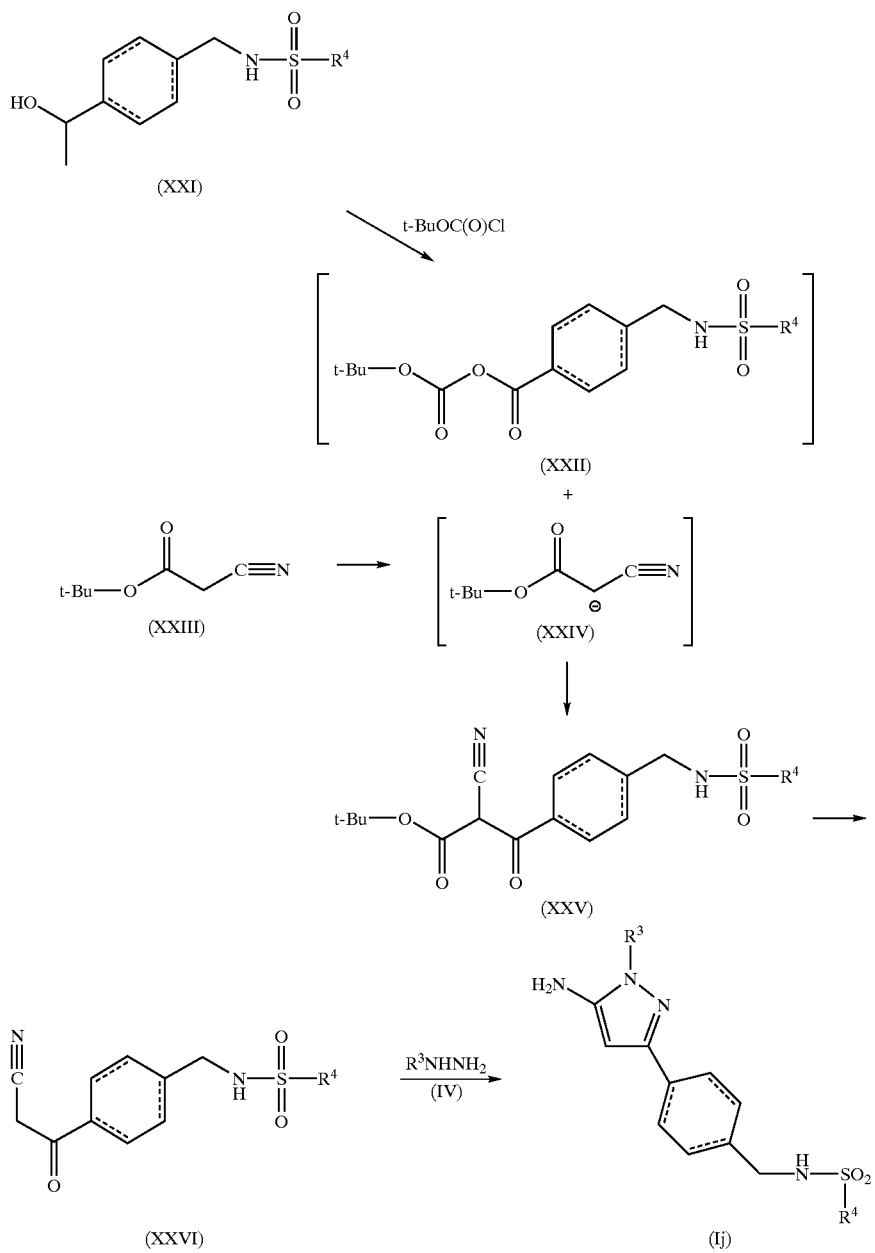

Accordingly, a compound of formula (XXI), wherein the symbol

represents -phenyl- or -cyclohexyl-, a known compound or compound prepared by known methods, is reacted with t-butyl chloroformate to yield the corresponding mixed anhydride of formula (XXII).

An α-nitrile of formula (XXII), a known compound, is reacted with a base such as NaH, KH, NaOCH$_3$, and the like, to produce the corresponding anion of formula (XXIV).

The mixed anhydride of formula (XXII) is reacted with the anion of formula (XXIV), at ambient temperature, to yield the corresponding α-nitrile-β-ketone of formula (XXV).

The compound of formula (XXV) is deprotected by removing the t-butoxycarbonyl (BOC) protecting group with an acid such as trifluoroacetic acid (TFA), hydrochloric acid, and the like, to produce the corresponding compound of formula (XXVI).

The compound of formula (XXVI) is coupled with a suitably substituted hydrazine of formula (IV), in the presence of a base such as triethylamine (TEA), diisopropylethylamine (DIPEA), and the like, with heating from ambient temperature to reflux, to yield the corresponding aminopyrazole of formula (Ij).

Preferably, when L is -cyclohexyl- the compound of formula (XXI) is present in the trans configuration, resulting in the trans isomer of the compound of formula (Ij).

It is generally preferred that the respective product of each process step be separated from other components of the reaction mixture and then subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halohydrocarbon solvents. In those cases wherein the product is isolated as the acid addition salt the free base is obtained by techniques known to those skilled in the art.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (–)-di-p-toluoyl-d-tartaric acid and/or (+)-di-p-toluoyl-I-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The term "halogen" shall include iodine, bromine, chlorine and fluorine.

The term "alkyl" shall mean straight or branched chain alkanes of one to six carbon atoms, or any number within this range. For example, alkyl radicals include, methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Similarly, "alkenyl" and "alkynyl" groups include straight and branched chain alkenes and alkynes having 2 to 8 carbon atoms, or any number within this range.

The term "alkoxy" shall denote an oxygen ether radical of the above described straight or branched chain alkyl groups. For example, methoxy, ethoxy, n-propoxy, sec-butoxy, t-butoxy, n-hexyloxy and the like.

The term "aryl" indicates aromatic groups such as phenyl and naphthyl.

The term "aralkyl" means a $C_1$–$C_6$ alkyl group substituted with an aryl group (e.g., benzyl, phenylethyl). Similarly, the term "aralkenyl" means a $C_2$–$C_6$ alkenyl group substituted with an aryl group.

The term "heteroaryl" as used herein represents a stable five or six membered monocyclic aromatic ring system or a nine or ten membered benzo-fused heteroaromatic ring system which consists of carbon atoms and from one to three heteroatoms selected from N, O or S. The heteroaryl group may be attached at any heteroatom or carbon atom which results in the creation of a stable structure. Examples of heteroaryl groups include, but are not limited to pyridyl, pyrimidinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, indazolyl, indolyl, benzothiazolyl, benzothiadiazolyl, benzotriazolyl, quinolinyl or isoquinolinyl. Preferred heteroaryl groups include pyridyl, pyrimidinyl, thiazolyl, imidazolyl, benzimidazolyl, quinolinyl and isoquinolinyl.

The term "cycloalkyl" as used herein shall represent a stable 3–8 membered monocyclic, saturated ring system, for example cyclopentyl, cyclohexyl, and the like. Similarly, the term "heterocycloalkyl" shall represents a stable 3–8 membered monocyclic or 9–10 membered bicyclic, saturated or partially unsaturated ring system containing one to three heteroatoms selected from the group consisting of N, O and S. Suitable examples of heterocycloalkyl groups include, but are not limited to pyrrolidinyl, pyrazolidinyl, piperidinyl, piperazinyl, dioxanyl, morpholinyl, dithienyl, thiomorpholinyl, 1,3,4-trihydroisoquinolinyl, 2,3,4-trihydroquinolinyl, 1,2,3,4-tetrahydroquinolinyl, 1,2,3,4-tetrahydroisoquinolinyl, and the like. The heterocycloalkyl may be attached at any heteroatom or carbon atom which results in the creation of a stable structure.

The term "carbonyl" shall denote

The term "amino" shall mean —$NH_2$. The term "carbonylamino" shall denote

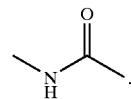

The term, "aminocarbonyl" shall denote

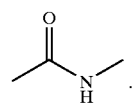

The term "sulfonylamino" shall denote

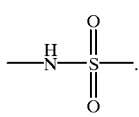

-continued

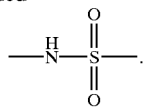

The term "cyclic secondary amine" shall denote any ring structure containing a N atom and capable of binding at the nitrogen atom. Suitable examples include 1,2,3,4-tetrahydroisoquinolinyl, 1,2,3,4-tetrahydroquinolinyl, morpholinyl, piperidinyl, and the like.

The term "di(unsubstituted or substituted arylsulfonyl) amino", shall denote an amine group substituted with two arylsulfonyl groups, where the aryl sulfonyl group may be optionally substituted and wherein the two arylsulfonyl groups and the optional substituents on the aryl sulfonyl groups are identical. Suitable examples include di(phenylsulfonyl)amino, di(napthylsulfonyl)amino, di(methylphenylsulfonyl)amino, di(methoxyphenylsulfonyl)amino, di(trifluoromethoxyphenylsulfonyl)amino di(fluorophenylsulfonyl)amino, di(trifluoromethylphenylsulfonyl)amino, di((ditrifluoromethyl)phenylsulfonyl)amino, di((methylcarbonylamino)phenylsulfonyl)amino, di(dimethylamino)phenylsulfonyl)amino, and the like.

Under standard nomenclature used throughout this disclosure, the terminal portion of the designated side chain is described first, followed by the adjacent functionality toward the point of attachment. Thus, for example, a "phenylC$_1$–C$_6$ alkylaminocarbonylC$_1$–C$_6$alkyl" substituent refers to a group of the formula

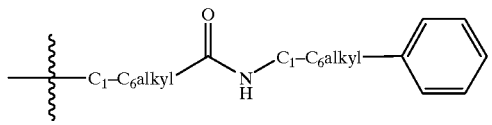

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

When a particular group is "substituted" (e.g., aryl, heteroaryl, cycloalkyl, heterocycloalkyl), that group may have one or more substituents, preferably from one to five substituents, more preferably from one to three substituents, most preferably from one to two substituents, independently selected from the list of substituents.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The present invention therefore provides a method of treating a condition selected from an eating disorder, obesity, bulimia nervosa, diabetes, binge eating, anorexia nervosa, dyslipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea, in a subject in need thereof, which comprises administering any of the compounds as defined herein, in a quantity effective to treat said condition. The compound may be administered to a patient by any conventional route of administration, including, but not limited to, intravenous, oral, subcutaneous, intramuscular, intradermal and parenteral. The quantity of the compound that is effective for treating a condition as described above is between 0.1 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating a condition selected from eating disorder, obesity, bulimia nervosa, diabetes, binge eating, anorexia nervosa, dyslipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea, described in the present invention may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of the central nervous system is required.

The daily dosage of the products may be varied over a wide range from 5 to 1,000 mg per adult human per day. For oral administration, the compositions are preferably provided in the form of tablets containing, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.1 mg/kg to about 20 mg/kg of body weight per day. Preferably, the range is from about 0.2 mg/kg to about 10 mg/kg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

For the treatment of disorders of the central nervous system, the pharmaceutical compositions described herein will typically contain from 1 to about 1000 mg of the active ingredient per dosage; one or more doses per day may be administered. Determination of optimum doses and frequency of dosing for a particular disease state or disorder is within the experimental capabilities of those knowledgeable in the treatment of central nervous system disorders. The preferred dose range is 1–100 mg/kg.

As modulators of the NPY5 receptor, the compounds of Formula I are useful for treating feeding disorders such as obesity, anorexia nervosa and bulimia nervosa, and abnormal conditions such as epilepsy, depression, anxiety and sexual/reproductive disorders in which modulation of the NPY5 receptor may be useful. The compounds compete with the endogenous ligands NPY and PYY and possibly non-endogenous ligands, and bind to the NPY5 receptor. In addition, the compounds demonstrate antagonist activity by antagonizing the action of NPY upon binding to the Y5 receptor.

The compounds described herein are ligands of the NPY5 receptor, but are not necessarily limited solely in their pharmacological or biological action due to binding to this or any neuropeptide, neurotransmitter or G-protein coupled receptor. For example, the described compounds may also undergo binding to dopamine or serotonin receptors. The compounds described herein are potentially useful in the regulation of metabolic and endocrine functions, particularly those associated with feeding, and as such, may be useful for the treatment of obesity. In addition, the compounds described herein are potentially useful for modulating other endocrine functions, particularly those controlled by the pituitary and hypothalamic glands, and therefore may be useful for the treatment of inovulation/infertility due to insufficient release of luteinizing hormone (LH).

The present invention comprises pharmaceutical compositions containing one or more of the compounds of Formula (I).

Abbreviations used in the specification, particularly the Schemes and Examples, are as follows:

| | |
|---|---|
| Ar = | Aryl group |
| BSA = | Bovine Serum Albumin |
| DCE = | Dichloroethane |
| DIPEA = | Diisopropylethylamine |
| DMAP = | 4-N,N-Dimethylaminopyridine |
| DMF = | N,N-Dimethylformamide |
| DMSO = | Dimethylsulfoxide |
| D$_2$O = | Deuterated water |
| EDTA = | Ethylene Diamine Tetraacetic Acid |
| Et$_3$N = | Triethylamine |
| Et$_2$O = | Diethyl ether |
| EtOAc = | Ethyl acetate |
| EtOH = | Ethanol |
| HATU = | O-(7-Azabenzotriazol-1-yl)-N,N,N",N"-Tetramethyl Uronium Hexafluorophosphate |
| HEPES = | 4-(2-Hydroxyethyl)-1-Piperizine Ethane Sulfonic Acid |
| HOBT = | 1-Hydroxybenzotriazole |
| HPLC = | High Pressure Liquid Chromatography |
| NaOEt = | Sodium Ethoxide |
| PBS = | Phosphate Buffered Saline |
| Pd—C = | Palladium on Carbon Catalyst |
| Ph = | Phenyl |
| RT or rt = | Room temperature |
| t-BOC = | Tert-Butoxycarbonyl |
| TEA = | Triethylamine |
| TFA = | Trifluoroacetic Acid |
| THF = | Tetrahydrofuran |
| TLC = | Thin Layer Chromatography |
| Tris HCl = | Tris[hydroxymethyl]aminomethyl hydrochloride |

The following examples describe the invention in greater detail and are intended to illustrate the invention, but not to limit it. All compounds were identified by a variety of methods including nuclear magnetic resonance spectroscopy, mass spectrometry and in some cases, infrared spectroscopy and elemental analysis. Nuclear magnetic resonance (300 MHz NMR) data is reported in parts per million downfield from tetramethylsilane. Mass spectra data is reported in mass/charge (m/z) units. Unless otherwise noted, the materials used in the example were obtained from readily available commercial sources or synthesized by standard methods known to those skilled in the art.

EXAMPLE 1

N-[4-5-amino-1-(4-methyl phenyl)-1H-pyrazol-3-yl]phenyl]-4-methoxy-benzenesulfonamide (36)

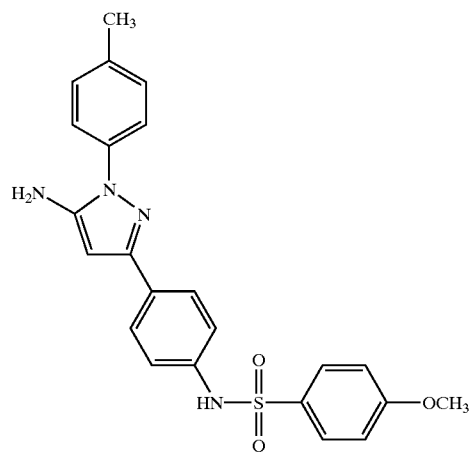

A. To a solution of 2-bromo-4'-nitroacetophenone (30 g, 0.123 mol) in ethanol (200 mL) at 0° C. was added a solution of NaCN (18 g, 0.368 mol) in H$_2$O (60 mL) dropwise over 1 h. Upon completion of the addition, the mixture was stirred at 0° C. for an additional hour and then diluted with H$_2$O (200 mL). The solution was treated with 1N aq. HCl solution, to a pH of 2, and extracted with CH$_2$Cl$_2$ (2×500 ML). The combined organic layers were dried over Na$_2$SO$_4$ and concentrated by rotary evaporation. The residue was purified by flash chromatography on silica gel eluting with 1:1 hexane/EtOAc to obtain 2-cyano-4'nitroacetophenone as an orange solid.

$^1$H NMR (300 MHz, CDCl$_3$) δ 4.16 (s, 2H), 8.12 (d, 2H, J=9 Hz), 8.39 (d, 2H, J=8.14 Hz).

B. To a solution of 2-cyano-4'nitroacetophenone in ethanol (100 mL) at room temperature was added tolylhydrazine (6.44 g, 0.04 mol) and triethylamine (15.4 mL, 0.11 mol). The resulting solution was heated to reflux and maintained at reflux for 1 h. The solution was cooled to room temperature at which time EtOAc (500 mL) was added. The organic solution was washed with brine (2×500 mL), dried over Na$_2$SO$_4$ and concentrated by rotary evaporation. The residue was purified by column chromatography on silica gel eluting with 1:1 hexane/EtOAc to yield 1-(4-tolyl)-3-(4-nitrophenyl)-5-aminopyrazole as a solid.

$^1$H NMR (300 MHz, CDCl$_3$) δ 2.43 (s, 3H), 6.05 (s, 1H), 7.34 (d, 2H, J=8.57 Hz), 7.48 (d, 2H, J=7.71 Hz), 7.98 (d, 2H, J=9 Hz), 8.25 (d, 2H, J=9.42 Hz).

C. To a solution of 1-(4-tolyl)-3-(4-nitrophenyl)-5-aminopyrazole (0.48 g, 1.6 mmol) in EtOAc (50 mL) at room temperature was added 10% Pd-C (0.1 g). The mixture was treated with hydrogen gas at 30 psi for 30 min. on a Parr shaker. The mixture was filtered through Celite and the solvent removed by rotary evaporation to yield 1-(4-tolyl)-3-(4-aminophenyl)-5-aminopyrazole as an oil, which was used without further purification.

$^1$H NMR (300 MHz, CDCl$_3$) δ 2.38 (s, 3H), 5.86 (s, 1H), 6.70 (d, 2H, J=8.57 Hz), 7.28 (d, 2H, J=9.0 Hz), 7.50 (d, 2H, J=7.71 Hz), 7.62 (d, 2H, J=8.57 Hz).

D. To a solution of 1-(4-tolyl)-3-(4-aminophenyl)-5-aminopyrazole (0.6 g, 2.27 mmol) in THF (20 mL) and H$_2$O (8 mL) at room temperature was added 4-methoxybenzenesulfonyl chloride (0.94 g, 4.55 mmol) and potassium carbonate (0.95 g, 6.88 mmol). The mixture was stirred at room temperature overnight and was then partitioned between H$_2$O (20 mL) and EtOAc (100 mL). The layers were separated and the organic layer was dried over Na$_2$SO$_4$ and concentrated. The residue was purified by preparatory TLC, eluting with 2:1 hexanes/EtOAc to yield N-[4-5-amino-1-(4-methylphenyl)-1H-pyrazol-3-yl]phenyl]-4-methoxy benzenesulfonamide.

$^1$H NMR (300 MHz, CDCl$_3$) δ 2.37 (s, 3H), 3.75 (s, 3H), 5.83 (s, 1H), 6.82 (d, 2H, J=8.85 Hz), 7.05 (d, 2H, J=8.37 Hz), 7.22 (d, 2H, J=6.48 Hz), 7.43 (d, 2H, J=8.13 Hz), 7.65 (t, 4H, J=8.68 Hz, 8.99 Hz).

EXAMPLE 2

N-[4-[5-amino-1(4-methylphenyl)-1H-pyrazol-3-yl] phenyl]-N-(phenylsulfonyl)-benzenesulfonamide (22)

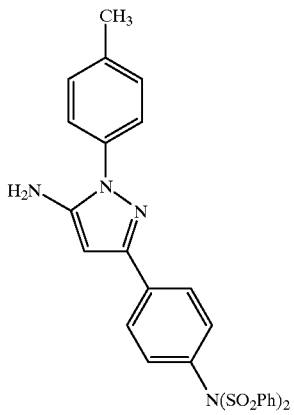

To a solution of 1-(4-tolyl)-3-(4-aminophenyl)-5-aminopyrazole (0.1 g, 0.4 mmol) in CH$_2$Cl$_2$ (5 mL) at room temperature was added triethylamine (0.16 mL, 1.2 mmol) and benzenesulfonyl chloride (0.11 mL, 0.82 mmol). The resultant mixture was stirred at room temperature overnight. The solvent was evaporated and the residue purified by prep TLC eluting with 2:1 hexanes/EtOAc to yield N-[4-[5-amino-1(4-methylphenyl)-1H-pyrazol-3-yl]phenyl]-N-(phenylsulfonyl)-benzenesulfonamide as a solid.

$^1$H NMR (300 MHz, CDCl$_3$) δ 2.42 (s, 3H), 5.96 (s, 1H), 7.02 (d, 2H, J=8.57 Hz), 7.30 (d, 2H, J=9.0 Hz), 7.49 (d, 2H, J=8.57 Hz), 7.56 (t, 3H, J=7.28 Hz, 7.70 Hz), 7.68 (t, 3H, J=5.14 Hz, 6.01 Hz), 7.79 (d, 2H, J=8.14 Hz), 7.95 (d, 4H, J=8.67 Hz).

EXAMPLE 3

N-[4-[5-amino-1-(4-methylphenyl)-1H-pyrazol-3-yl] phenyl]-4-methoxy-benzamide (53)

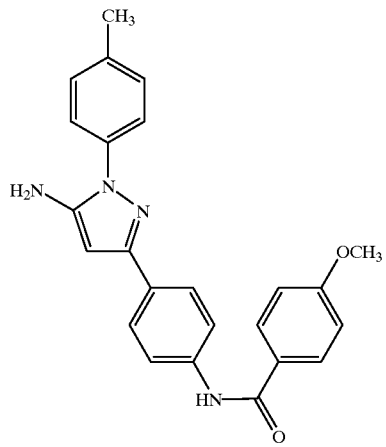

To a solution of diamine 1-(4-tolyl)-3-(4-aminophenyl)-5-aminopyrazole (0.05 g, 0.17 mmol) in CH$_2$Cl$_2$ (5 mL) at room temperature was added triethylamine (0.05 mL, 0.36 mmol) and 4-methoxybenzoyl chloride (0.035 g, 0.2 mmol). The resulting mixture was stirred at room temperature overnight. The solvent was evaporated and the residue purified by preparatory TLC, eluting with 1:1 EtOAc/hexanes to obtain N-[4-[5-amino-1-(4-methylphenyl)-1H-pyrazol-3-yl]phenyl]-4-methoxy-benzamide as a solid.

$^1$H NMR (300 MHz, CDCl$_3$) δ 2.41 (s, 3H), 3.88 (s, 3H), 5.96 (s, 1H), 6.98 (d, 2H, J=8.68 Hz), 7.30 (d, 2H, J=7.28 Hz), 7.50 (d, 2H, J=8.24 Hz), 7.66 (d, 2H, J=8.62 Hz), 7.83 (m, 4H).

EXAMPLE 4

4-(methylamino)-N-[4-[5-(methylamino)-1-(4-methylphenyl)-1H-pyrazol-3-yl]phenyl]-benzensulfonamide (75)

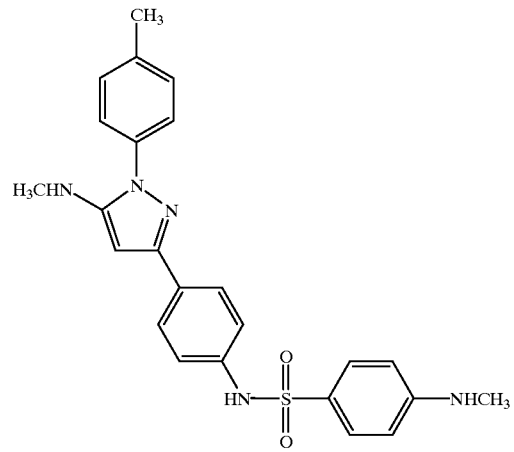

A. To a solution of diamine 1-(4-tolyl)-3-(4-aminophenyl)-5-aminopyrazole (0.65 g, 2.5 mmol) in THF (10 mL) and H$_2$O (2 mL) at room temperature was added 4-nitrobenzenesulfonyl chloride (0.82 g, 3.7 mmol) and potassium carbonate (1.02 g, 7.2 mmol). The reaction mixture was stirred at room temperature overnight. The mixture was partitioned between H$_2$O (20 mL) and EtOAc (50 mL) and the organic layer was separated, dried over Na$_2$SO$_4$ and concentrated. The residue was purified by column chromatography eluting with 1:1 hexane/EtOAc to obtain 1-(4-tolyl)-3-(4'-(4-nitrophenyl) sulfonylamino phenyl)-5-aminopyrazole as a solid. MS 450.1 (MH$^+$).

B. To a solution of 1-(4-tolyl)-3-(4'-(4-nitrophenyl) sulfonylamino phenyl)-5-aminopyrazole (0.8 g, 1.8 mmol) in EtOAc (30 mL) at room temperature was added 10% Pd-C (0.2 g). The mixture was treated with hydrogen gas at 30 psi for 4 h on a Parr shaker. The mixture was filtered through Celite and the solvent evaporated to yield 1-(4-tolyl)-3-(4'-(4-aminophenyl)sulfonylamino phenyl)-5-aminopyrazole as a solid, which was used without further purification.

$^1$H NMR (300 MHz, CDCl$_3$) δ 2.40 (s, 3H), 5.87 (s, 1H), 6.57 (d, 2H, J=8.14 Hz), 7.09 (d, 2H, J=8.65 Hz), 7.33 (d, 2H, J=7.71 Hz), 7.45 (m, 4H), 7.58 (d, 2H, J=8.57 Hz).

C. To a solution of 1-(4-tolyl)-3-(4'-(4-aminophenyl) sulfonylamino phenyl)-5-aminopyrazole (0.07 g, 0.34 mmol) in acetonitrile (5 mL) at room temperature was added 37% formaldehyde in H$_2$O (0.028 mL, 0.34 mmol), acetic acid (0.01 mL) and NaCNBH$_3$ (0.02 g, 0.34 mmol). The mixture was stirred at room temperature overnight. The mixture was diluted with saturated aqueous NaHCO$_3$ solution (10 mL) and extracted with EtOAc (50 mL). The organic layer was separated, dried over Na$_2$SO$_4$ and concentrated. The residue was purified by column chromatography, eluting with 1:1 hexanes/EtOAc to give 4-(methylamino)-N-[4-[5-(methylamino)-1-(4-methylphenyl)-1H-pyrazol-3-yl]phenyl]-benzensulfonamide.

$^1$H NMR (300 MHz, CDCl$_3$) δ 2.40 (s, 3H), 2.83 (d, 3H, J=4.28 Hz), 2.89 (d, 3H, J=4.71 Hz), 5.80 (s, 1H), 6.45 (d, 2H, J=9.43 Hz), 6.45 (d, 2H, J=9.43 Hz), 7.07 (d, 2H, J=8.14 Hz), 7.28 (d, 2H, J=6.85 Hz), 7.44 (d, 2H, J=8.50 Hz), 7.53 (d, 2H, J=8.57 Hz), 7.72 (d, 2H, J=8.15 Hz).

EXAMPLE 5

5-amino-N-5-isoquinolinyl-1-[3-(trifluormethyl) phenyl]-1H-pyrazole-3-carboxamide (79)

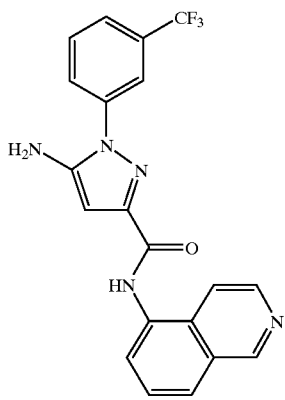

A. To Et$_2$O (70 mL) in a dried 300 mL round-bottom flask at 0° C. was added 21% NaOEt in ETOH (13.4 mL, 0.17 mol), diethyl oxalate (25 g, 0.17 mol) and acetonitrile (8.9 mL, 0.17 mol). The reaction mixture was heated to room temperature and stirred, at room temperature, overnight. The precipitate was collected by vacuum filtration, dried in a vacuum oven for 6 h and used without further purification.

B. To a suspension of the precipitate from step A above (1 g, 6.1 mmol) in CHCl$_3$ (10 mL) at room temperature was added H$_2$O (10 mL), 3-trifluoromethylphenyl hydrazine (1.07 g, 6.1 mmol) and concentrated H$_2$SO$_4$ (0.33 mL). The resulting two phase mixture was stirred at room temperature for 72 h. The layers were separated and the organic layer was washed with saturated aqueous NaHCO$_3$ (2×50 mL) and dried over Na$_2$SO$_4$ and concentrated. The residue was purified by column chromatography, eluting with 25% EtOAc/hexanes to yield 1-(3-trifluormethylphenyl)-3-ethoxycarbonyl-5-aminopyrazole.

$^1$H NMR (300 MHz, CDCl$_3$) δ 1.40 (t, 3H, J=7.7 Hz), 4.40 (q, 2H, J=7.7 Hz), 7.23 (m, 1H), 7.42 (m, 2H), 7.51 (s, 1H), 8.48 (s, 1H).

C. To a solution of 1-(3-trifluormethylphenyl)-3-ethoxycarbonyl-5-aminopyrazole (2.06 g, 6.8 mmol) in EtOH (50 ml) and H$_2$O (100 mL) at room temperature was added NaOH (450 mg, 10.2 mmol). The solution was heated to reflux and let stir at reflux for 2 h. The solution was cooled to room temperature and the EtOH was evaporated. The aqueous solution was treated with concentrated HCl to pH 2. EtOAc (150 mL) was added and the layers were separated. The aqueous layer was extracted with EtOAc (3×100 mL). The combined organic layers were dried over Na$_2$SO$_4$ and concentrated to yield 1-(3-trifluoromethylphenyl)-3-carboxy-5-aminpyrazole, which was used without further purification.

$^1$H NMR (300 MHz, CDCl$_3$) δ 6.15 (s, 1H), 7.65 (m, 2H), 7.84 (m, 1H), 7.95 (m, 2H).

D. To a solution of 1-(3-trifluoromethylphenyl)-3-carboxy-5-aminpyrazole (100 mg, 0.37 mmol) in DMF (3 mL) at room temperature was added DIPEA (0.13 mL, 0.74 mmol), HATU (154 mg, 0.41 mmol), and 5-aminoquinoline (64 mg, 0.44 mmol). The resulting solution was stirred at room temperature overnight. The solution was concentrated and the residue purified by column chromatography, eluting with 10% EtOAc/hexanes/1% Et$_3$N to obtain pyrazole 5-amino-N-5-isoquinolinyl-1-[3-(trifluormethyl)phenyl]-1H-pyrazole-3-carboxamide as a solid.

$^1$H NMR (300 MHz, CDCl$_3$) δ 6.30 (s, 1H), 7.70 (m, 1H), 7.72 (m, 2H), 7.82 (m, 2H), 7.84 (m, 1H), 7.95 (m, 1H), 8.40 (d, 1H, J=8.5 Hz), 8.52 (d, 1H, J=6.8 Hz), 9.22 (s, 1H).

EXAMPLE 6

N-Phenyl-4-[1-phenyl-5-[(phenylsulfonyl)amino]-1H-pyrazol-3-yl]benzamide (4)

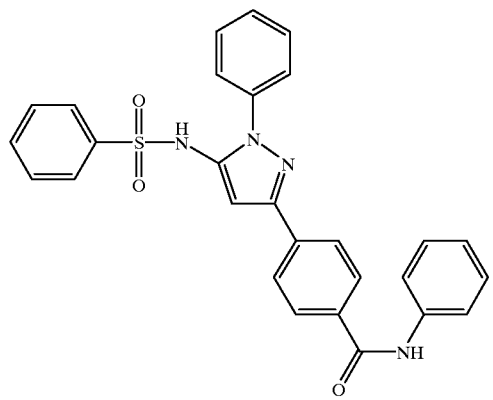

A. A mixture of methyl-4-(cyanoacetyl)benzoate (5.0 g, 24.6 mmol) and phenylhydrazine (2.42 ml, 24.6 mmol) in ethanol (100 ml) was heated to reflux for 20 hours. The mixture was cooled and the product was collected by filtration. The product was purified by trituration in hot acetonitrile, cooled and collected by filtration to give the product 4-(5-amino-1-phenyl-1H-pyrazole-3-yl)-benzoic acid methyl ester as a colorless solid.

$^1$H NMR(DMSO-d$_6$, 300 MHz) δ 3.87 (s, 3H), 5.54 (s, 2H, exchanges with D$_2$O), 6.03 (s, 1H), 7.38 (t, 1H), 7.54 (t, 2H), 7.69 (d, 2H), 7.93 (d, 2H), 8.00 (d, 2H); MS 294 (MH$^+$).

B. A solution of benzenesulfonyl chloride (0.913 ml, 7.15 mmol) in dichloromethane (7 ml) was added slowly to a solution of 4-(5-amino-1-phenyl-1H-pyrazole-3-yl)-benzoic acid methyl ester (1.5 g, 5.11 mmol) in pyridine (20 ml) at 5° C. The resulting solution was stirred at room temperature for 18 h. The solvent was evaporated in vacuo and the products were separated by flash chromatography, on silica gel, using 0 to 2% methanol in dichloromethane as the eluant, to yield 4-(5-benzenesulfonylamino-1-phenyl-1H-pyrazole-3-yl)-benzoic acid methyl ester, and 4-{5-[bis(Benzenesulfonyl)amino]-1-phenyl-1H-pyrazole-3-yl}-benzoic acid methyl ester.

$^1$H NMR(CDCl$_3$, 300 MHz) δ 3.94 (s, 3H), 6.33 (s, 1H), 7.32–7.51 (m, 7H), 7.63–7.70 (m, 4H), 7.77 (d, 4H), 7.82 (d, 2H) and 8.08 (d, 2H); MS 572 (M—H$^-$).

C. A mixture of 4-{5-[bis(Benzenesulfonyl)amino]-1-phenyl-1H-pyrazole-3-yl}-benzoic acid methyl ester (1.0 g, 1.74 mmol) and lithium hydroxide monohydrate (1.0 g, 23.8 mmol) in methanol (20 ml) was stirred at room temperature for 2.5 days. The solvent was evaporated in vacuo, and the residue was dissolved in water (20 ml). The solution was neutralized with concentrated hydrochloric acid to give a white precipitate. The solid was collected by filtration, washed with water and dried in vacuo to yield 4-(5-benzenesulfonylamino-1-phenyl-1H-pyrazole-3-yl)-benzoic acid as a solid.

$^1$H NMR(DMSO-d$_6$, 300 MHz) δ 6.54 (s, 1H), 7.40–7.60 (m, 7H), 7.64–7.73 (m, 3H), 7.90 (d, 2H) and 7.98 (d, 2H); MS 418 (M—H$^-$).

D. Benzotriazol-1-yloxytripyrrolid inophosphonium hexafluorophosphate (0.136 g, 0.26 mmol) was added to a solution of 4-(5-benzenesulfonylamino-1-phenyl-1H-pyrazole-3-yl)-benzoic acid (0.10 g, 0.24 mmol) and N,N-diisopropylethylamine (0.062 ml, 0.36 mmol) in N,N-dimethylformamide (2 ml). 1-Hydroxybenzotriazole hydrate (30 mg, 0.24 mmol) and 4-(N,N-dimethylamino) pyridine (catalytic) were added and the resulting solution was stirred at room temperature for 3 hours. Water (7 ml) was added, and a precipitate was collected by filtration and washed with water. The solid was purified by preparative thin layer silica gel chromatography, using 2% methanol in dichloromethane as the eluant, to yield N-Phenyl-4-[1-phenyl-5-[(phenylsulfonyl)amino]-1H-pyrazol-3-yl]benzamide as a colorless solid.

$^1$H NMR (DMSO-d$_6$, 300 MHz) δ 6.57 (s, 1H), 7.11 (t, 1H), 7.32–7.83 (m, 14H), 7.94 (d, 2H) and 8.02 (d, 2H); MS 493 (M—H$^-$).

EXAMPLE 7 trans-N-[[4-[5-Amino-1-[4-tolyl]-1H-pyrazol-3-yl]cyclohexyl]methyl]-2-naphthylsulfonamide (82)

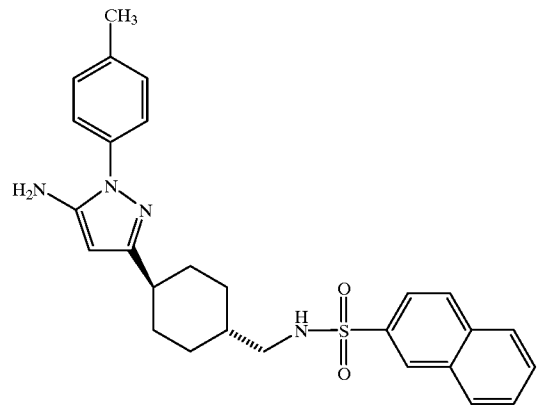

A. trans-4-(2-Naphthylsulfonylamino)methylcyclohexane carboxylic acid (2.57 g, 7.40 mmol) was suspended in dichloroethane (DCE) (25 mL) in a round-bottom flask under a dry nitrogen atmosphere at room temperature. Triethylamine (1.68 mL, 12.0 mmol) was added with vigorous stirring, resulting in dissolution of the suspension. Isobutylchloroformate (1.56 mL, 12.0 mmol) was added in a rapid dropwise fashion and the reaction was then stirred for an additional 45 min. Tetrahydrofuran (10 mL) was added to facilitate stirring of the suspension. The reaction was stirred for an additional 30 min at ambient temperature yielding the Boc-protected mixed anhydride as a solid.

B. In a separate round-bottom flask, freshly-distilled t-butyl cyanoacetate (3.58 mL, 25.0 mmol) was dissolved in anhydrous tetrahydrofuran (25 mL) under a dry nitrogen atmosphere. Sodium hydride (0.72 g of 80% oil dispersion, 24.0 mmol) was added with caution and the mixture was stirred at ambient temperature for 75 min to yield the corresponding cyanoacetate anion in solution.

C. The crude reaction containing the Boc-protected mixed anhydride was added to the cyanoacetate anion at room temperature and the resulting mixture was stirred overnight (14 h). Ethyl acetate (200 mL) was then added to the reaction, the mixture was transferred to a separatory funnel and washed twice with hydrochloric acid (50 mL, 1M aqueous solution). The aqueous extracts were combined and extracted with fresh ethyl acetate (1×50 mL). The organic extracts were combined and washed with brine (1×50 mL), dried (MgSO$_4$), filtered and the solvents removed in vacuo to afford a pale orange oil. The oil was dissolved in a minimum amount of DCE and purified via a silica gel plug, eluting with DCE to remove excess cyanoacetate. The desired sulfonylamino-ketoester was obtained as a peach-colored solid.

$^1$H NMR (CDCl$_3$): δ 0.95 (m, 2H), 1.50 (s, 9H), 1.80–1.90 (m, 4H), 3.60 (m, 1H), 3.82 (app t, 2H), 3.76 (app s, 2H), 4.88 (m, 1H), 7.63 (m, 2H), 7.80–8.05 (m, 4H), 8.45 (s, 1H), 13.95 (s, 1H); MS 471 (M+H)$^+$, 941 (2M+H$^+$).

D. Sulfonylamino-ketoester (4.0 g) was dissolved in a mixture of trifluoroacetic acid and DCE (25 mL of a 2:1 v/v solution) and stirred at ambient temperature for 14 h. The volatile components were removed by rotary evaporation to afford the alpha-cyanoketosulfonamide as a pale orange oil. The product was used in subsequent reaction steps without further purification.

The cyanoketosulfonamide was dissolved in ethanol (50 mL) in a round-bottom flask at room temperature. Triethylamine (5.6 mL, 40 mmol) was added followed by addition of p-tolylhydrazine hydrochloride (1.9 g, 12 mmol) and the mixture was heated at reflux for 2.5 h. After cooling, the solvent was removed by rotary evaporation. Ethyl acetate (300 mL) was added and the mixture was transferred to a separatory funnel, washed with hydrochloric acid (3×50 mL) and then washed with brine (1×50 mL). The organics were dried ($MgSO_4$), filtered and the solvents removed by rotary evaporation to yield a dark oil. A minimum amount of ethyl acetate was added to initiate precipitation of a yellow solid which was removed by filtration.

The solid was determined to contain two major components in a 6:1 ratio ($R_f$=3.5 (major) and $R_f$=4.0 (minor); HPLC were obtained on a Hewlett Packard HP1050 using a gradient (10:90 to 90:10) of acetonitrile/water with 0.1% trifluoroacetic acid as eluent and UV detection at 220 and 255 nM). The solid was then purified by a series of flash silica gel columns; the first one being eluted with 20:1 DCE/isopropanol and the second one being eluted with a gradient of 1% $Et_3N$ in 1:1 Hexane/EtOAc to pure EtOAc. The resultant yellow solid was then dissolved in a minimum amount of hot toluene and the resulting solutions decanted from trace amounts of insoluble material. Upon cooling and the addition of hexanes, trans-N-[[4-[5-Amino-1-[4-tolyl]-1H-pyrazol-3-yl]cyclohexyl]methyl]-2-naphthylsulfonamide precipitated as a yellow solid.

$^1$H NMR ($CDCl_3$, 300 MHz): δ 0.95–1.05 (m, 2H), 1.29–1.43 (m, 2H), 1.49–1.56 (m, 1H), 1.80–1.88 (m, 2H), 1.97–2.03 (m, 2H), 2.39 (s, 3H), 2.49 (m, 1 H), 2.83 (dd, 2H), 3.73, (bs, 2H), 4.83 (m, 1H), 5.40 (s, 1H), 7.18–7.29 (m, 3H), 7.40 (m, 1H), 7.63 (m, 2H), 7.78–7.88 (2d, 2H), 7.98 (m, 2H), 8.48 (s, 1H); MS 475 $(M+H)^+$.

EXAMPLE 8

In Vitro Assays

NPY5 HTS Centrifugation Assay

The compounds described in this invention were evaluated for binding to the human neuropeptide Y5 receptor.

Stable Transfection

The human NPY5 receptor cDNA (Genbank Accession number U66275) was inserted into the vector pClneo (Invitrogen) and transfected into human embryonic kidney cells (HEK-293) via Calcium phosphate method (Cullen 1987). Stably transfected cells were selected with G-418 (600 ug/mL). Stably transfected cells served as the source for the membranes for the NPY5 receptor binding assay.

Membrane Preparation

NPY5-transfected HEK293 cells were grown to confluence in 150 $cm^2$ culture dishes. Cells were washed once with phosphate-buffered saline (Gibco Cat# 14040-133). Cells were then incubated in phosphate-buffered saline without Calcium and without Magnesium, supplemented with 2 mM EDTA. Cells were incubated for 10 minutes at room temperature and the cells were collected by repetitive pipetting. Cells were formed into pellets and frozen at −80 until needed. Frozen pellets were homogenized with a polytron at full speed for 12 seconds in a homogenization buffer (20 mM Tris HCl, 5 mM EDTA, pH 7.4). Homogenates were centrifuged for 5 minutes at 4° C. at 200 g. Supernatants were transferred to corex tubes and centrifuged for 25 minutes at 28,000 g. Pellets were re-suspended in Binding (20 mM HEPES, 10 mM NaCl, 0.22 mM $KH_2PO_4$, 1.3 mM $CaCl_2$, 0.8 mM $MgSO_4$, pH 7.4). Membranes were kept on ice until use.

A competition binding assay, known to those skilled in the art, was used in which the test compounds (aminopyrazoles of formula (I) compete with $^{125}$I-PYY for binding to cell membranes. In simple terms, less $^{125}$I-PYY bound to the membranes implies that the test compound is a good inhibitor (competitor). Bound $^{125}$I-PYY is determined by centrifugation the membranes, aspirating supernatant, washing away residual $^{125}$I-PYY and subsequently counting the bound sample in a γ-counter.

Procedure for Radioligand Binding Assay

Compounds to be tested were prepared as 10× stocks in binding buffer and added first to assay tubes (RIA vials, Sarstedt). Twenty (20) μL of each 10× compound stock was pipetted into vials and 80 μL of $^{125}$I-PYY (NEN catalog number NEX240), which had been diluted to a concentration of 200 pM in 0.25% BSA in binding buffer, was added to the compound tubes (final concentration of $^{125}$I-PYY is 80 pM). To each tube was added 100 μL of membranes and the mixture was agitated by pipetting 2 times. Samples were incubated for 1 hr at room temperature. Aluminum cast plates (Sarstedt) containing the vials were centrifuged 10 minutes at 3200 rpm in a Sorvall RT6000. Supernatant was then aspirated. To each vial was added 400 μL PBS and the vial was then aspirated again. Vials were put in carrier polypropylene 12×75 tube and counted in gamma counter (Packard). Non-specific binding was determined in the presence of 300 nM NPY. Percent inhibition of $^{125}$I-PYY binding was calculated by subtracting non-specific binding from the test samples (compounds of formula (I)), taking these counts and dividing by total binding, and multiplying by 100. Inhibitory concentration values ($IC_{50}$) of compounds that show appreciable inhibition of $^{125}$I-PYY binding were calculated by obtaining percent inhibition of $^{125}$I-PYY binding values at different concentrations of the test compound, and using a graphing program such as GraphPad Prism (San Diego, Calif.) to calculate the concentration of test compound that inhibits fifty-percent of $^{125}$I-PYY binding (Table 2). These operations are known to those skilled in the art.

Following the procedures set forth herein, the compounds listed in Tables 1 to 6 were prepared.

TABLE 1

| No | R² | R³ | X | R⁴ |
|---|---|---|---|---|
| 1 | 4-methylphenyl-SO₂- | 2-methylphenyl | -NH-SO₂- | 4-methylphenyl |
| 2 | 4-methylphenyl-SO₂- | 4-methylphenyl | -NH-SO₂- | 4-methylphenyl |
| 4 | phenyl-SO₂- | phenyl | -C(O)-NH- | phenyl |
| 5 | phenyl-SO₂- | phenyl | -C(O)-NH- | 4-fluorophenyl |
| 6 | phenyl-SO₂- | phenyl | -C(O)-NH- | 4-methylphenyl |
| 7 | H | phenyl | -C(O)-O- | methyl |
| 10 | phenyl-SO₂- | phenyl | -C(O)-NH- | benzyl |
| 11 | phenyl-SO₂- | phenyl | -C(O)-NH- | 1-napthyl |
| 12 | phenyl-SO₂- | phenyl | -C(O)-NH- | 2-napthyl |
| 13 | phenyl-SO₂- | phenyl | -C(O)- | 2-methyl-1,2,3,4-tetrahydroisoquinolinyl |

TABLE 1-continued
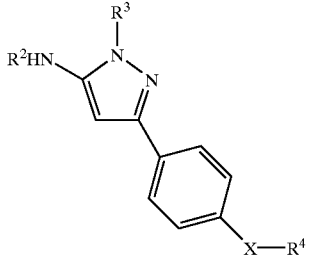
| No | R² | R³ | X | R⁴ |
|---|---|---|---|---|
| 14 | 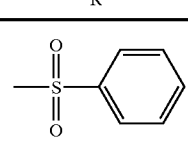 | phenyl | 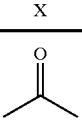 | 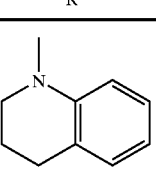 |
| 15 | 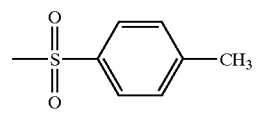 | 4-methylphenyl | 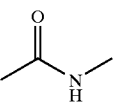 | phenyl |
| 16 | 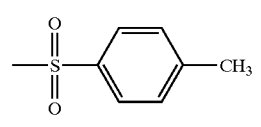 | 4-methylphenyl | 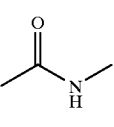 | 4-fluorophenyl |
| 17 | 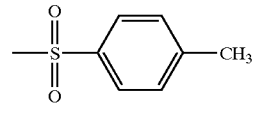 | 4-methylphenyl | 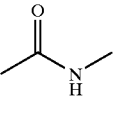 | 4-methylphenyl |
| 18 | 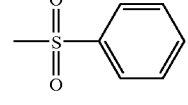 | phenyl | 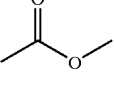 | methyl |
| 19 | H | 4-methylphenyl | 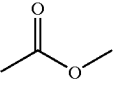 | methyl |
| 31 | H | 4-methylphenyl | 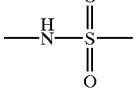 | 4-methylphenyl |
| 33 | H | 4-methylphenyl | 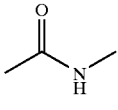 | 4-methylphenyl |
| 34 | 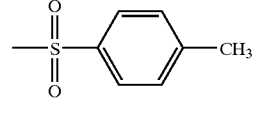 | 4-methylphenyl | 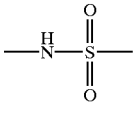 | 4-methylphenyl |
| 36 | H | 4-methylphenyl | 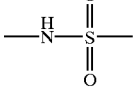 | 4-methoxyphenyl |

TABLE 1-continued

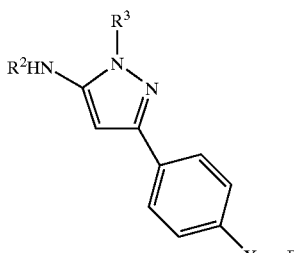

| No | R² | R³ | X | R⁴ |
|---|---|---|---|---|
| 37 | H | 4-methylphenyl | —NH—S(=O)₂— | phenyl |
| 38 | H | 4-methylphenyl | —NH—S(=O)₂— | 4-fluoro phenyl |
| 39 | H | 4-methylphenyl | —NH—S(=O)₂— | 3-trifluoro methylphenyl |
| 41 | H | 4-methylphenyl | —NH—S(=O)₂— | 3,5-di(trifluoro methyl)phenyl |
| 42 | H | 4-methylphenyl | —NH—S(=O)₂— | 4-trifluoro methoxyphenyl |
| 43 | H | 4-methylphenyl | —NH—S(=O)₂— | 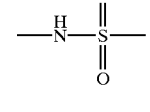 |
| 44 | H | 4-methylphenyl | —NH—S(=O)₂— | 1-napthyl |
| 45 | H | 4-methylphenyl | —NH—S(=O)₂— | 2-napthyl |
| 47 | H | 4-methylphenyl | —NH—S(=O)₂— | 4-trifluoro methylphenyl |
| 48 | H | 4-methylphenyl | —NH—S(=O)₂— | 3,4-di(methoxy) phenyl |

TABLE 1-continued

| No | R² | R³ | X | R⁴ |
|---|---|---|---|---|
| 49 | H | 1-napthyl | —NH—S(=O)₂— | 4-methoxyphenyl |
| 50 | H | 4-methylphenyl | —NH—S(=O)₂— | 4-bromophenyl |
| 51 | H | 4-methylphenyl | —NH—S(=O)₂— | 4-nitrophenyl |
| 52 | H | 4-methylphenyl | —NH—S(=O)₂— | 4-aminophenyl |
| 53 | H | 4-methylphenyl | —NH—C(=O)— | 4-methoxyphenyl |
| 54 | H | 2-pyridyl | —NH—S(=O)₂— | 4-methoxyphenyl |
| 55 | H | 2-pyridyl | —NH—S(=O)₂— | phenyl |
| 56 | H | 2-pyridyl | —NH—S(=O)₂— | 4-fluorophenyl |
| 57 | H | 2-pyridyl | —NH—S(=O)₂— | 3-trifluoromethylphenyl |
| 60 | H | 1-napthyl | —NH—S(=O)₂— | phenyl |

TABLE 1-continued

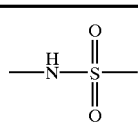

| No | R² | R³ | X | R⁴ |
|----|----|----|---|----|
| 61 | H | 4-methylphenyl | 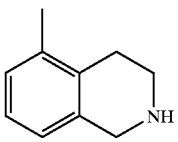 | 5-methyl-1,2,3,4-tetrahydroisoquinolin-yl |
| 62 | H | 4-methylphenyl | 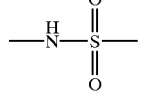 | 3-nitrophenyl |
| 63 | H | 4-methylphenyl | 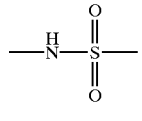 | 2-nitrophenyl |
| 64 | H | 4-methylphenyl | 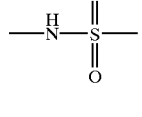 | 2-aminophenyl |
| 65 | H | 4-methylphenyl | 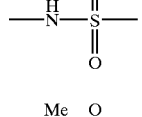 | 3-aminophenyl |
| 70 | H | 4-methylphenyl | 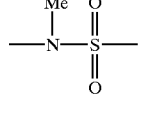 | 4-methoxyphenyl |
| 71 | H | 3-methylphenyl | 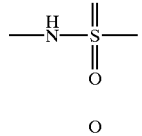 | 4-methoxyphenyl |
| 72 | H | 3-methylphenyl | 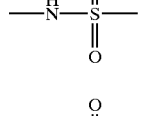 | phenyl |
| 73 | H | 3-methylphenyl | 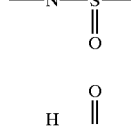 | 3-trifluoromethylphenyl |
| 74 | methyl | 4-methylphenyl | 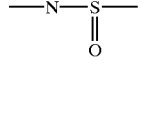 | 4-dimethylaminophenyl |

TABLE 1-continued

Structure: R²HN-[pyrazole with R³ on N1]-[phenyl]-X-R⁴

| No | R² | R³ | X | R⁴ |
|---|---|---|---|---|
| 75 | methyl | 4-methylphenyl | —NH—S(=O)₂— | 4-methyl aminophenyl |
| 76 | H | 4-methylphenyl | —NH—S(=O)₂— | 4-dimethyl aminophenyl |
| 80 | H | 4-methylphenyl | —N(CH₂CH₂OMe)—S(=O)₂— | 4-methoxyphenyl |
| 81 | H | 4-methylphenyl | —NH—S(=O)₂— | 3-dimethyl aminophenyl |
| 84 | H | phenyl | —NH—S(=O)₂— | 4-methoxyphenyl |
| 85 | H | 5-CF₃-2-methylpyridin-yl | —NH—S(=O)₂— | 4-methoxyphenyl |
| 86 | H | 4-CF₃-2-methylpyrimidin-yl | —NH—S(=O)₂— | 4-methoxyphenyl |
| 87 | H | 3-di(methyl) aminophenyl | —NH—S(=O)₂— | 4-methoxyphenyl |
| 88 | H | 3-dimethyl aminophenyl | —NH—S(=O)₂— | phenyl |

TABLE 1-continued
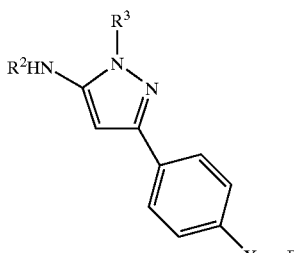
| No | R² | R³ | X | R⁴ |
|----|----|----|---|----|
| 89 | H | 3,5-di(trifluoromethyl)phenyl | —N(H)—S(O)₂— | 4-methoxyphenyl |
| 90 | H | 3,5-di(trifluoromethyl)phenyl | —N(H)—S(O)₂— | phenyl |
| 91 | H | 4-fluorophenyl | —N(H)—S(O)₂— | 4-methoxyphenyl |
| 92 | H | 4-fluorophenyl | —N(H)—S(O)₂— | phenyl |
| 93 | H | phenyl | —N(H)—S(O)₂— | phenyl |
| 94 | H | 3,5-di(trifluoromethyl)phenyl | —CH₂—N(H)—S(O)₂— | phenyl |
TABLE 2
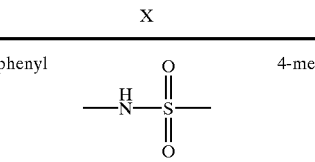
| No | R³ | X | R⁴ |
|----|----|---|----|
| 66 | 4-methylphenyl | —N(H)—S(O)₂— | 3-nitrophenyl |
| 67 | 4-methylphenyl | —N(H)—S(O)₂— | 4-methoxyphenyl |

TABLE 2-continued

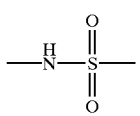

| No | R³ | X | R⁴ |
|---|---|---|---|
| 68 | 4-methylphenyl | —N(H)—S(=O)₂— | phenyl |
| 69 | 4-methylphenyl | —N(H)—S(=O)₂— | 3-trifluoromethylphenyl |

TABLE 3

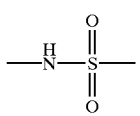

| No. | R³ | X | R⁴ |
|---|---|---|---|
| 77 | 4-methylphenyl | —CH₂—N(H)—S(=O)₂— | 2-napthyl |
| 82 | 3-trifluoromethyl phenyl | —CH₂—N(H)—S(=O)₂— | 2-nitrophenyl |
| 83 | 3-trifluoromethyl phenyl | —CH₂—N(H)—S(=O)₂— | 2-aminophenyl |

TABLE 4

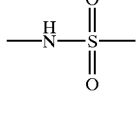

| No | R¹ | R² | R³ | X | R⁴ |
|---|---|---|---|---|---|
| 8 | phenyl sulfonyl | —S(=O)₂—phenyl | phenyl | —C(=O)—O— | methyl |
| 9 | H | —S(=O)₂—phenyl | phenyl | —C(=O)—O— | H |
| 20 | 4-methyl phenyl sulfonyl | —S(=O)₂—(4-methylphenyl) | 4-methylphenyl | —C(=O)—O— | methyl |

TABLE 4-continued

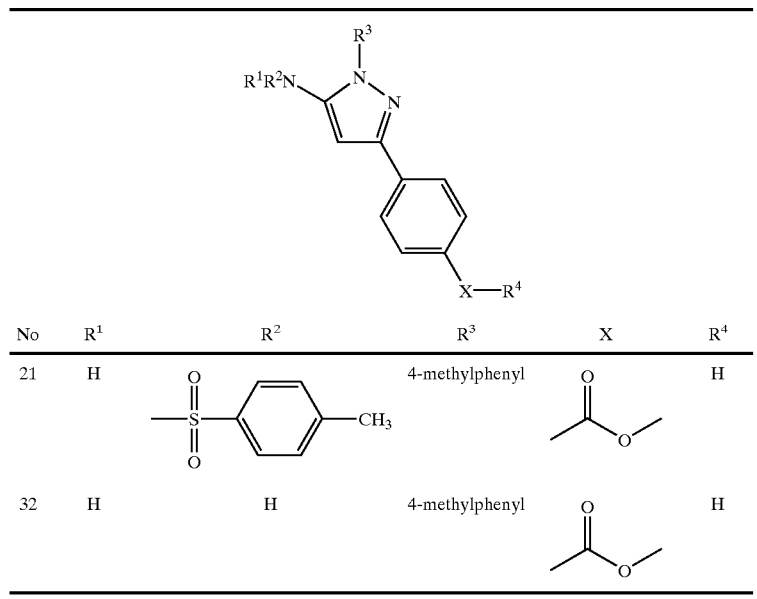

| No | R¹ | R² | R³ | X | R⁴ |
|----|----|----|----|----|----|
| 21 | H | (methylsulfonyl-4-methylphenyl) | 4-methylphenyl | (acetoxy) | H |
| 32 | H | H | 4-methylphenyl | (acetoxy) | H |

TABLE 5

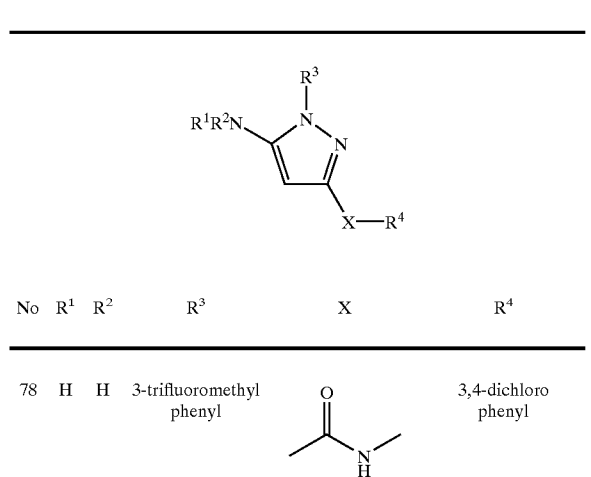

| No | R¹ | R² | R³ | X | R⁴ |
|----|----|----|----|----|----|
| 78 | H | H | 3-trifluoromethyl phenyl | (N-methylacetamide) | 3,4-dichloro phenyl |
| 79 | H | H | 3-trifluoromethyl phenyl | (N-methylacetamide) | 5-methylisoquinoline |

TABLE 6

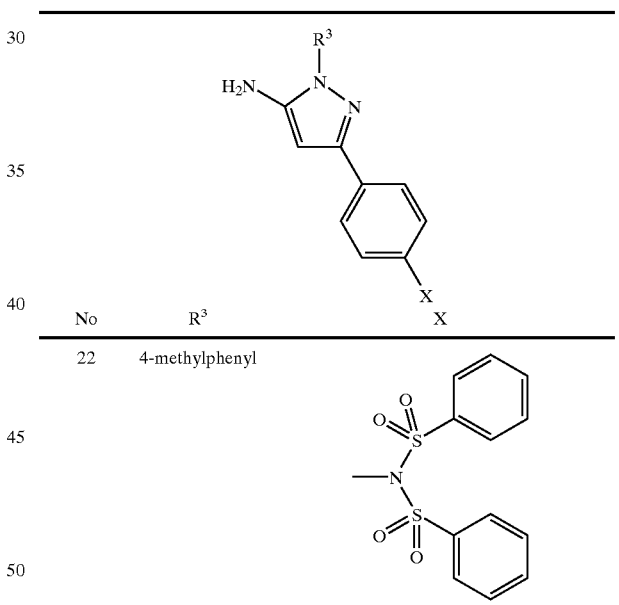

| No | R³ | X |
|----|----|----|
| 22 | 4-methylphenyl | N-methyl-N,N-bis(phenylsulfonyl) |
| 23 | 4-methylphenyl | N-methyl-N,N-bis(4-fluorophenylsulfonyl) |

TABLE 6-continued

![Structure: 5-amino-1-R³-3-(4-X-phenyl)pyrazole]

| No | R³ | X |
|----|----|----|
| 24 | 4-methylphenyl | -N(SO₂-C₆H₄-4-Me)₂ (methyl on N, two 4-methylphenylsulfonyl groups) |
| 25 | 4-methylphenyl | -N(Me)(SO₂-C₆H₄-4-OMe)₂ |
| 26 | 4-methylphenyl | -N(Me)(SO₂-C₆H₄-3-CF₃)₂ |
| 27 | 4-methylphenyl | -N(Me)(SO₂-2-naphthyl)₂ |
| 28 | 4-methylphenyl | -N(Me)(SO₂-C₆H₄-4-NHAc)₂ |
| 29 | 4-methylphenyl | -N(Me)(SO₂-C₆H₄-4-OCF₃)₂ |
| 30 | 4-methylphenyl | -N(Me)(SO₂-C₆H₄-4-NMe₂)₂ |
| 35 | 4-methylphenyl | -N(Me)(SO₂-1-naphthyl)₂ |

Mass spectral and in vitro binding affinities for the selected compounds of formula (I) are provided in Table 7.

TABLE 6-continued

| No | R³ | X |
|---|---|---|
| 40 | 4-methylphenyl | 3,5-bis(CF₃)-phenylsulfonyl-N-methyl-3,5-bis(CF₃)-phenylsulfonyl |
| 46 | 4-methylphenyl | 4-CF₃-phenylsulfonyl-N-methyl-4-CF₃-phenylsulfonyl |
| 58 | 2-pyridyl | 3-CF₃-phenylsulfonyl-N-methyl-3-CF₃-phenylsulfonyl |
| 59 | 2-pyridyl | 4-F-phenylsulfonyl-N-methyl-4-F-phenylsulfonyl |

TABLE 7

| Cmpd # | % Inh NPY5 @ 3 μM | IC₅₀ hNPY5 | Mass (calc'd) | Mass (obs) |
|---|---|---|---|---|
| 1 | | 200 nM | 572.71 | |
| 2 | | 34 nM | 572.71 | |
| 4 | 0.00 | | 494.57 | 493.0 |
|   |   |   |   | 495.1 |
| 5 | 0.00 | | 512.56 | 511.1 |
| 6 | 0.00 | | 508.60 | 507.1 |
| 7 | 13.00 | | 293.32 | 294.0 |
| 8 | 0 | | 573.65 | |
| 9 | 0 | | 419.46 | 418.1 |
| 10 | 19.00 | | 508.60 | 507.1 |
|    |       |   |        | 509.1 |
| 11 | 14.00 | | 544.63 | 545.1 |
| 12 | 2.00 | | 544.63 | 545.1 |
| 13 | 12.00 | | 534.64 | 535.1 |
| 14 | (26.00 @ 30 μM) | | 534.64 | 535.1 |
| 15 | 4.00 | | 522.63 | 521.1 |
| 16 | 1.00 | | 540.62 | 539.1 |
| 17 | 6.00 | | 536.65 | 535.1 |
| 18 | 2.00 | | 433.49 | 432.1 |
| 19 | 2.00 | | 307.35 | 308.0 |
| 20 | 0.00 | | 615.73 | 616.1 |
| 21 | 16.00 | | 447.51 | 446.1 |
| 22 | | 514 nM | 544.65 | 545.1 |
| 23 | | 30 μM | 580.63 | 581.1 |
| 24 | | 30 μM | 572.71 | 573.1 |
| 25 | | 30 μM | 604.71 | 605.1 |
| 26 | 16.00 | | 680.65 | 681.1 |
| 27 | 0.00 | | 644.77 | 645.1 |
| 28 | 21.00 | | 658.76 | 657.1 |
| 29 | 16.00 | | 712.65 | 713.1 |
| 30 | | 10 μM | 730.91 | 729.2 |
| 31 | | 28 nM | 418.52 | 419.3 |
| 32 | 0.00 | | 293.32 | 294.1 |
| 33 | 0.00 | | 382.46 | 383.2 |
| 34 | | 6 μM | 572.71 | 573.0 |
| 35 | 29.00 | | 644.77 | 645.1 |
| 36 | 100.00 | 15 nM | 434.52 | 435.2 |
| 37 | 97.00 | 25 nM | 404.49 | 405.2 |
| 38 | 98.00 | 29 nM | 422.48 | 423.2 |
| 39 | 95.00 | 31 nM | 472.49 | 473.1 |
| 40 | 16.00 | | 816.64 | 816.9 |
| 41 | 10.00 | | 540.49 | 541.1 |
| 42 | 94.00 | 67 nM | 488.49 | 489.1 |
| 43 | 62.00 | | 455.54 | 456.1 |
| 44 | 72.00 | | 454.55 | 455.1 |
| 45 | 90.00 | 208 nM | 454.55 | 455.1 |
| 46 | 21.00 | | 680.65 | 681.0 |
| 47 | 82.00 | 63 nM | 472.49 | 473.1 |
| 48 | 76.00 | 839 nM | 464.54 | 465.2 |
| 49 | | 48 nM | 470.55 | 471.1 |
| 50 | | 58 nM | 483.39 | 485.0 |
| 51 | | 79 nM | 449.49 | 540.1 |
| 52 | | 74 nM | 419.51 | 420.3 |
| 53 | 0.00 | | 398.46 | 399.1 |
| 54 | | 436 nM | 421.48 | 422.1 |
| 55 | | 458 nM | 391.45 | 392.1 |
| 56 | | 217 nM | 409.44 | 410.1 |
| 57 | | 289 nM | 459.45 | 460.2 |
| 58 | 0.00 | | 667.61 | 668.0 |
| 59 | 0.00 | | 567.60 | 568.0 |
| 60 | | 233 nM | 440.53 | 441.1 |
| 61 | 0.00 | | 459.57 | 460.1 |
| 62 | | 21 nM | 449.49 | 450.0 |
| 63 | | 178 nM | 449.49 | 450.1 |
| 64 | | 229 nM | 419.51 | 420.0 |
| 65 | | 303 nM | 419.51 | 420.1 |
| 66 | 0.00 | | 449.49 | 450.1 |
| 67 | 85.00 | | 434.52 | 435.3 |
| 68 | | 169 nM | 404.49 | |
| 69 | 20.00 | | 472.49 | 433.4 |
| 70 | 59.00 | | 448.54 | 449.5 |
| 71 | | 37 nM | 434.52 | 435.1 |

TABLE 7-continued

| Cmpd # | % Inh NPY5 @ 3 μM | IC$_{50}$ hNPY5 | Mass (calc'd) | Mass (obs) |
|---|---|---|---|---|
| 72 | | 38 nM | 404.49 | 405.1 |
| 73 | | 23 nM | 472.49 | |
| 74 | | 487 nM | 461.59 | 462.3 |
| 75 | | 40 nM | 447.56 | 448.2 |
| 76 | | 162 nM | 447.56 | 448.2 |
| 77 | | 243 nM | 474.63 | |
| 78 | 81.00 | | 415.20 | 415.3, 417.3, 419.2 |
| 79 | | 400 nM | 397.36 | 398.1 |
| 80 | 68.00 | | 492.60 | 493.5 |
| 81 | | 145 nM | 447.56 | 448.41 |
| 82 | | 24 nM | 523.53 | |
| 83 | | 20 nM | 493.55 | |
| 84 | | 100 nM | 420.49 | 421.13 |
| 85 | 38.00 | | 489.48 | 490.29 |
| 86 | | 709 nM | 490.46 | 491.16 |
| 87 | | 30 nM | 463.56 | 464.15 |
| 88 | | 22 nM | 433.53 | 434.16 |
| 89 | 48.00 | | 556.49 | 557.11 |
| 90 | | 683 nM | 526.46 | 527.07 |
| 91 | | 37 nM | 438.48 | 439.07 |
| 92 | | 28 nM | 408.46 | 409.18 |
| 93 | | 38 nM | 390.47 | 391.15 |
| 94 | | 114 nM | 472.49 | 473.10 |

What is claimed:

1. A compound of the formula (I):

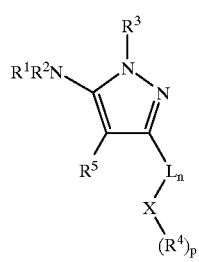

(I)

wherein $R^1$ and $R^2$ are each independently selected from the group consisting of hydrogen, $C_1$–$C_6$alkyl, sulfonylamino, and unsubstituted or substituted arylsulfonyl; wherein the substituents on the arylsulfonyl are one or more independently selected from halogen, $C_1$–$C_6$alkyl, $C_1$–$C_6$alkoxy, trifluoromethyl or trifluoromethoxy;

$R^3$ is selected from the group consisting of unsubstituted or substituted aryl and unsubstituted or substituted heteroaryl; wherein the substituents on the aryl or heteroaryl are one or more independently selected from halogen, $C_1$–$C_6$alkyl, $C_1$–$C_6$alkoxy, trifluoromethyl, trifluoromethoxy, amino, $C_1$–$C_6$alkylamino or di($C_1$–$C_6$alkyl) amino;

L is selected from the group consisting of unsubstituted or substituted aryl, unsubstituted or substituted heteroaryl and $C_3$–$C_8$cycloalkyl; wherein the substituents on the aryl or heteroaryl are one or more independently selected from halogen, $C_1$–$C_4$alkyl or trifluoromethyl;

n is an integer selected from 0 or 1;

X is selected from the group consisting of sulfonylamino, aminocarbonyl, carbonyl, carbonylamino, sulfonyl,

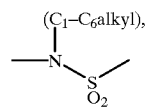

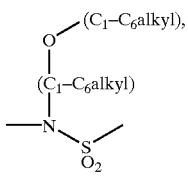

sulfonylamino$C_1$–$C_6$alkyl and $C_1$–$C_6$alkylaminosulfonyl; and p is 1;

alternatively X is selected from the group consisting of di(unsubstituted or substituted arylsulfonyl)amino; wherein the substituents on the aryl group are one or more independently selected from halogen, $C_1$–$C_6$alkyl, $C_1$–$C_6$alkoxy, trifluoromethyl, trifluoromethoxy, $C_1$–$C_6$alkylcarbonylamino, amino, $C_1$–$C_6$alkylamino or di($C_1$–$C_6$alkyl)amino, and wherein the two aryl groups of the di(unsubstituted or substituted arylsulfonyl)amino have the same substitution pattern; and p is 0;

$R^4$ is selected from the group consisting of unsubstituted or substituted aryl, $C_1$–$C_6$aralkyl, unsubstituted or substituted heteroaryl and unsubstituted or substituted heterocycloalkyl; wherein the substituents on the aryl, heteroaryl or heterocycloalkyl are one or more independently selected from halogen, $C_1$–$C_6$alkyl, $C_1$–$C_6$alkoxy, trifluoromethyl, trifluoromethoxy, amino, $C_1$–$C_6$alkylamino, di ($C_1$–$C_6$alkyl)amino, nitro or cyano;

$R^5$ is hydrogen;

provided that when $R^1$ and $R^5$ are both hydrogen, and $R^3$ is phenyl, or methylphenyl, and n is 1, and L is phenyl, and X is sulfonylamino, and $R^2$ is methylphenylsulfonyl, then $R^4$ is selected from the group consisting of unsubstituted or substituted aryl, wherein the substituents on the aryl are one or more independently selected from halogen, $C_1$–$C_6$alkoxy, trifluoromethyl, trifluoromethoxy, amino, $C_1$–$C_6$alkylamino, di ($C_1$–$C_6$alkyl)amino, nitro or cyano; $C_1$–$C_6$aralkyl, unsubstituted or substituted heteroaryl and unsubstituted or substituted heterocycloalkyl; wherein the substituents on the heteroaryl or heterocycloalkyl are one or more independently selected from halogen, $C_1$–$C_6$alkyl, $C_1$–$C_6$alkoxy, trifluoromethyl, trifluoromethoxy, amino, $C_1$–$C_6$alkylamino, di ($C_1$–$C_6$alkyl) amino, nitro or cyano;

and pharmaceutically acceptable salts thereof.

2. The compound of claim 1 wherein $R^1$ is hydrogen;

$R^2$ is selected from the group consisting of hydrogen, $C_1$–$C_4$alkyl, and unsubstituted or substituted arylsulfonyl; wherein the substituents on the arylsulfonyl are one to three substituents independently selected from halogen or $C_1$–$C_4$alkyl;

$R^3$ is selected from the group consisting of unsubstituted or substituted aryl and unsubstituted of substituted heteroaryl; wherein the substituents on the aryl or heteroaryl are one to three substituents independently selected from halogen, $C_1$–$C_4$alkyl, trifluoromethyl, amino, $C_1$–$C_6$alkylamino or di($C_1$–$C_6$alkyl) amino;

L is selected from the group consisting of unsubstituted or substituted aryl and $C_3$–$C_8$cycloalkyl; wherein the substituents on the aryl are one to three substituents independently selected from halogen, $C_1$–$C_4$alkyl or trifluoromethyl;

X is selected from the group consisting of sulfonylamino, aminocarbonyl, carbonyl, carbonylamino,

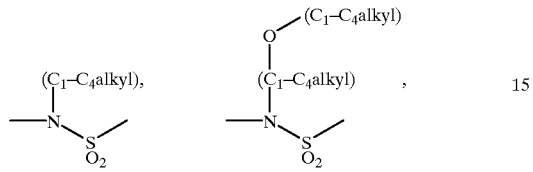

and sulfonylamino$C_1$–$C_4$alkyl; and p is 1;

alternatively, X is selected from the group consisting of di(unsubstituted or substituted arylsulfonyl)amino; wherein the substituents on the aryl group are one or two substituents independently selected from halogen, $C_1$–$C_4$alkyl, $C_1$–$C_4$alkoxy, trifluoromethyl, trifluoromethoxy, $C_1$–$C_4$alkylcarbonylamino or di($C_1$–$C_4$alkyl)amino; and where the two aryl groups have the same substitution pattern; and p is 0;

$R^4$ is selected from the group consisting of unsubstituted or substituted aryl, $C_1$–$C_3$aralkyl, heteroaryl and heterocycloalkyl; wherein the substituents on the aryl are one or two substituents independently selected from halogen, $C_1$–$C_4$alkyl, $C_1$–$C_4$alkoxy, trifluoromethyl, trifluoromethoxy, amino, di ($C_1$–$C_4$alkyl)amino or nitro;

$R^5$ is hydrogen;

provided that when $R^3$ is phenyl, or methylphenyl, and n is 1, and L is phenyl, and X is sulfonylamino, and $R^2$ is methylphenylsulfonyl, then $R^4$ is selected from the group consisting of unsubstituted or substituted aryl, $C_1$–$C_3$aralkyl, heteroaryl and heterocycloalkyl; wherein the substituents on the aryl are one or two substituents independently selected from halogen, $C_1$–$C_4$alkoxy, trifluoromethyl, trifluoromethoxy, amino, di($C_1$–$C_4$alkyl)amino or nitro;

and pharmaceutically acceptable salts thereof.

3. The compound of claim 2 wherein $R^2$ is selected from the group consisting of hydrogen, methyl, phenylsulfonyl and methylphenylsulfonyl;

$R^3$ is selected from the group consisting of phenyl, napthyl, fluorophenyl, methylphenyl, trifluoromethylphenyl, 3,5-di (trifluoromethyl)phenyl, dimethylaminophenyl, pyridyl, 2- (5-trifluoromethyl) pyridyl and 2- (4-trifluoromethyl)pyrimidyl;

L is selected from the group consisting of phenyl and cyclohexyl;

X is selected from the group consisting of sulfonylamino, aminocarbonyl, carbonyl, carbonylamino, sulfonyl (methyl) amino, sulfonyl(2-methoxyethyl)amino and sulfonylaminomethyl; and p is 1;

alternatively X is selected from the group consisting of di(phenylsulfonyl)amino, di(naphthylsulfonyl)amino and di(substituted phenylsulfonyl)amino; where the substituents on the phenyl group are one or two substituents independently selected from halogen, methyl, methoxy, trifluoromethyl, trifluoromethoxy, methylcarbonylamino or di(methyl)amino; and where the two phenyl groups have the same substitution pattern; and p is 0;

$R^4$ is selected from the group consisting of phenyl, benzyl, substituted phenyl, napthyl, isoquinolinyl, quinolinyl, 2-(1,2,3,4-tetrahydro)isoquinolinyl, 1-(1,2,3,4-tetrahydro)quinolinyl, and 5- (1,2,3,4-tetrahydro) isoquinolinyl; where the substituents on the phenyl are one or two substituents independently selected from halogen, methyl, methoxy, trifluoromethyl, trifuoromethoxy, amino, di(methyl)amino or nitro;

provided that when $R^3$ is phenyl, or methyiphenyl, and n is 1, and L is phenyl, and X is sulfonylamino, and $R^2$ is methylphenylsulfonyl, then $R^4$ is selected from the group consisting of phenyl, benzyl, substituted phenyl, napthyl, isoquinolinyl, quinolinyl, 2- (1,2,3,4-tetrahydro)isoquinolinyl, 1-(1,2,3,4-tetrahydro) quinolinyl, and 5-(1,2,3,4-tetrahydro)isoquinolinyl; where the substituents on the phenyl are one or two substituents independently selected from halogen, methoxy, trifluoromethyl, trifluoromethoxy, amino, di(methyl)amino or nitro;

and pharmaceutically acceptable salts thereof.

4. The compound of claim 3 wherein $R^2$ is selected from the group consisting of hydrogen and methyl;

$R^3$ is selected from the group consisting of 4-methylphenyl, 3-methylphenyl, 1-napthyl, 2-pyridyl, 3-trifluoromethylphenyl, phenyl, 2-(4-trifluoromethyl) pyrimidyl, 3-dimethylaminophenyl, 3,4-di (trifluoromethyl)phenyl and 4-fluorophenyl;

L is selected from the group consisting of

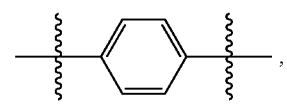,

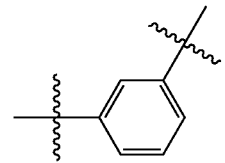

and

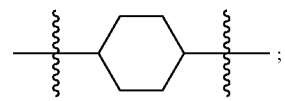;

X is selected from the group consisting of sulfonylamino, sulfonylaminomethyl and aminocarbonyl; and p is 1;

alternatively X is di(phenylsulfonyl)amino; and p is 0;

$R^4$ is selected from the group consisting of 4-methylphenyl, 4-methoxyphenyl, phenyl, 4-fluorophenyl, 3-trifluoromethylphenyl, 4-trifluoromethoxyphenyl, 2-napthyl, 3,4-dimethoxyphenyl, 4-bromophenyl, 4-nitrophenyl, 4-aminophenyl, 3-nitrophenyl, 2-nitrophenyl, 2-aminophenyl, 3-aminophenyl, 4-dimethylaminophenyl, 3-dimethylaminophenyl, 4-methylaminophenyl and 5-isoquinolinyl;

and pharmaceutically acceptable salts thereof.

5. The compound of claim 4 wherein $R^3$ is selected from the group consisting of 4-methylphenyl, 3-methylphenyl, 1-napthyl, 2-pyridyl, 3-trifluoromethylphenyl, phenyl, 3-dimethylaminophenyl and 4-fluorophenyl;

X is selected from the group consisting of sulfonylamino, sulfonylaminomethyl and aminocarbonyl;

$R^4$ is selected from the group consisting of 4-methylphenyl, 4-methoxyphenyl, phenyl, 4-fluorophenyl, 3-trifluoromethylphenyl, 4-trifluoromethoxyphenyl, 2-napthyl, 4-bromophenyl, 4-nitrophenyl, 4-aminophenyl, 3-nitrophenyl, 2-nitrophenyl, 2-aminophenyl, 3-aminophenyl, 4-dimethylaminophenyl, 3-dimethylaminophenyl, 4-methylaminophenyl, 5-isoquinolinyl;

p is 1;

and pharmaceutically acceptable salts thereof.

6. The compound of claim 5 wherein $R^3$ is selected from the group consisting of 4-methylphenyl, 3-methylphenyl, 1-napthyl, 3-trifluoromethylphenyl, phenyl, 3-dimethylaminophenyl and 4-fluorophenyl;

n is 1;

X is selected from the group consisting of sulfonylamino and sulfonylaminomethyl;

$R^4$ is selected from the group consisting of 4-methylphenyl, 4-methoxyphenyl, phenyl, 4-fluorophenyl, 3-trifluoromethylphenyl, 4-trifluoromethoxyphenyl, 4-bromophenyl, 4-nitrophenyl, 4-aminophenyl, 3-nitrophenyl, 2-nitrophenyl, 2-aminophenyl, 4-dimethylaminophenyl, 3-dimethylaminophenyl and 4-methylaminophenyl;

and pharmaceutically acceptable salts thereof.

7. The compound of claim 6 wherein

L is selected from the group consisting of

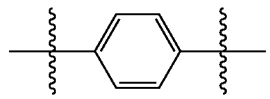

and

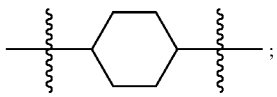

;

$R^4$ is selected from the group consisting of 4-methylphenyl, 4-methoxyphenyl, phenyl, 4-fluorophenyl, 3-trifluoromethylphenyl, 4-trifluoromethoxyphenyl, 4-bromophenyl, 4-nitrophenyl, 4-aminophenyl, 3-nitrophenyl, 2-nitrophenyl, 2-aminophenyl, and 4-methylaminophenyl;

and pharmaceutically acceptable salts thereof.

8. The compound of claim 7 wherein $R^4$ is selected from the group consisting of 4-methylphenyl, 4-methoxyphenyl, phenyl, 4-fluorophenyl, 3-trifluoromethylphenyl, 3-nitrophenyl, 2-nitrophenyl, 2-aminophenyl and 4-methylaminophenyl;

and pharmaceutically acceptable salts thereof.

9. The compound of claim 8 wherein $R^2$ is hydrogen;

$R^3$ is selected from the group consisting of 4-methylphenyl, 3-methylphenyl, 3-trifluoromethylphenyl and 3-dimethylaminophenyl;

$R^4$ is selected from the group consisting of 4-methoxyphenyl, phenyl, 3-trifluoromethylphenyl, 3-nitrophenyl, 2-nitrophenyl and 2-aminophenyl;

and pharmaceutically acceptable salts thereof.

10. The compound of claim 9 selected from the group consisting of 1-(4-methylphenyl)-3-(4-((4-methoxyphenyl)sulfonylamino)phenyl)-5-amino-1H-pyrazole; 1-(4-methylphenyl)-3-(4-(phenylsulfonylamino)phenyl)-5-amino-1H-pyrazole; 1-(4-methylphenyl)-3-(4-((3-nitrophenyl)sulfonylamino)phenyl)-5-amino-1H-pyrazole; 1-(3-methylphenyl)-3-(4-((3-trifluoromethylphenyl)sulfonylamino)phenyl)-5-amino-1H-pyrazole; 1-(3-trifluoromethylphenyl)-3-(4-((2-nitrophenyl)sulfonylaminomethyl)cyclohexyl)-5-amino-1H-pyrazole; 1-(3-trifluoromethylphenyl)-3-(4-((2-aminophenyl)sulfonylaminomethyl)cyclohexyl)-5-amino-1H-pyrazole; and 1-(3-dimethylaminophenyl)-3-(4-((4-methoxyphenyl)sulfonylamino)phenyl)-5-amino-1H-pyrazole; and pharmaceutically acceptable salts thereof.

11. A pharmaceutical composition comprising a compound of claim 1 and a pharmaceutically acceptable carrier.

12. A pharmaceutical composition made by mixing a compound of claim 1 and a pharmaceutically acceptable carrier.

13. A process for making a pharmaceutical composition comprising mixing a compound of claim 1 and a pharmaceutically acceptable carrier.

14. A method of treating a disorder mediated by the NPY Y5 receptor in a subject in need of such treatment comprising administering to the subject a therapeutically effective amount of a compound of claim 1.

15. The method of claim 14, wherein the therapeutically effective amount is between about 0.03 and about 300 mg/kg per day.

16. The method of claim 15, wherein the disorder is selected from an eating disorder, obesity, bulimia nervosa, diabetes, binge eating, anorexia nervosa, dyslipidimia, hypertension, memory loss, epileptic seizures, migraine, sleep disturbances, pain, infertility, depression, anxiety, cerebral hemorrhage, shock, congestive heart failure, nasal congestion or diarrhea.

17. A method of treating a disorder selected from an eating disorder, obesity, bulimia nervosa, diabetes, binge eating, anorexia nervosa, dyslipidimia, hypertension, memory loss, epileptic seizures, migraine, sleep disturbances, pain, infertility, depression, anxiety, cerebral hemorrhage, shock, congestive heart failure, nasal congestion or diarrhea in a subject in need thereof, comprising administering to the subject a therapeutically effective amount of a compound of claim 1.

18. The method of claim 17, wherein the therapeutically effective amount is between about 0.03 and about 300 mg/kg per day.

19. A method of treating a disorder mediated by the NPY Y5 receptor in a subject in need thereof comprising administering to the subject a therapeutically effective amount of the composition of claim 11.

20. A method of treating a disorder selected from an eating disorder, obesity, bulimia nervosa, diabetes, binge eating, anorexia nervosa, dyslipidimia, hypertension, memory loss, epileptic seizures, migraine, sleep disturbances, pain, infertility, depression, anxiety, cerebral hemorrhage, shock, congestive heart failure, nasal congestion or diarrhea in a subject in need thereof, comprising administering to the subject a therapeutically effective amount of the composition of claim 11.

* * * * *